(12) United States Patent
Kitane et al.

(10) Patent No.: US 9,345,420 B2
(45) Date of Patent: May 24, 2016

(54) MAGNETIC RESONANCE IMAGING APPARATUS

(71) Applicants: KABUSHIKI KAISHA TOSHIBA, Tokyo (JP); TOSHIBA MEDICAL SYSTEMS CORPORATION, Otawara-Shi (JP)

(72) Inventors: Shinichi Kitane, Nasushiobara (JP); Isao Tatebayashi, Utsunomiya (JP)

(73) Assignees: KABUSHIKI KAISHA TOSHIBA, Tokyo (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 0 days.

(21) Appl. No.: 13/767,265

(22) Filed: Feb. 14, 2013

(65) Prior Publication Data

US 2013/0211240 A1    Aug. 15, 2013

(30) Foreign Application Priority Data

Feb. 15, 2012    (JP) .................................. 2012-031047

(51) Int. Cl.
*A61B 5/05*        (2006.01)
*A61B 5/055*       (2006.01)
(Continued)

(52) U.S. Cl.
CPC ................. *A61B 5/055* (2013.01); *A61B 5/743* (2013.01); *A61B 5/7435* (2013.01); *G01R 33/56308* (2013.01); *A61B 5/0037* (2013.01); *A61B 5/4244* (2013.01)

(58) Field of Classification Search
CPC ...................................................... A61B 5/055
USPC .......................................... 600/431; 345/810
See application file for complete search history.

(56) References Cited

U.S. PATENT DOCUMENTS 6,198,957 B1 *    3/2001    Green ........................... 600/411
6,205,349 B1      3/2001    Kim et al.
(Continued)

FOREIGN PATENT DOCUMENTS

JP    04-261279      9/1992
JP    2000-116621    4/2000
(Continued)

OTHER PUBLICATIONS

Hashemi et al. "Chap.17 Scan parameters and image optimization" in "MRI: The Basis" (2010), Lippincott Williams and Wilkins, $3^{rd}$ edition, p. 1-9.*

(Continued)

*Primary Examiner* — Tse Chen
*Assistant Examiner* — Patrick M Mehl
(74) *Attorney, Agent, or Firm* — Oblon, McClelland, Maier & Neustadt, L.L.P

(57) ABSTRACT

A magnetic resonance imaging apparatus according to an embodiment is a magnetic resonance imaging apparatus that performs a contrast medium imaging, comprising a time management part that measures and manages a lapse time after injection of a contrast medium, a setting part that sets a start time of a second-half imaging in the form of a lapse time after injection of contrast medium, the second-half imaging being performed a predetermined idle time after a first-half imaging and the first-half imaging being performed after injection of the contrast medium, and a display part that displays at least the lapse time measured by the time management part and the start time set by the setting part.

15 Claims, 22 Drawing Sheets

(51) Int. Cl.
*A61B 5/00* (2006.01)
*G01R 33/563* (2006.01)

(56) References Cited

U.S. PATENT DOCUMENTS

| | | | |
|---|---|---|---|
| 6,643,534 B2 * | 11/2003 | Foo et al. | 600/420 |
| 7,565,651 B1 * | 7/2009 | Carey | 718/100 |
| 2003/0095150 A1 * | 5/2003 | Trevino et al. | 345/810 |
| 2004/0008028 A1 | 1/2004 | Horger et al. | |
| 2008/0211497 A1 * | 9/2008 | Iwadate et al. | 324/307 |
| 2009/0163797 A1 * | 6/2009 | Jurrissen et al. | 600/410 |
| 2011/0021904 A1 * | 1/2011 | Burrman | 600/420 |

FOREIGN PATENT DOCUMENTS

| | | |
|---|---|---|
| JP | 2004-041732 | 2/2004 |
| JP | 2005-144075 | 6/2005 |

OTHER PUBLICATIONS

Kellman et al. "Multicontrast delayed enhancement provides improved contrast between myocardial infarction and blood pool" (2005) J.Magn.Reson.Imaging 22(5):605-613.*
Tanimoto et al. "Consensus report of the 2nd international forum for liver MRI" (2009) Eur.Radiol. 19(supp.5):5975-5989.*
Hashemi et al 2010 MRI_the Basics_chapter 17 p. 1-9.*
Kellman et al. Multicontrast delayed engancement provides improved contrast between myocardial infarction and blood pool. 2005 J.Magn.Reson.Imaging 22:605-613.*
Tanimoto et al. Consensus report of the 2nd international forum for liver MR. 2009I Eur.Radiol. 19:S975-S989.*
Japanese Office Action issued Oct. 6, 2015 in Japanese Patent Application No. 2012-031047.

* cited by examiner

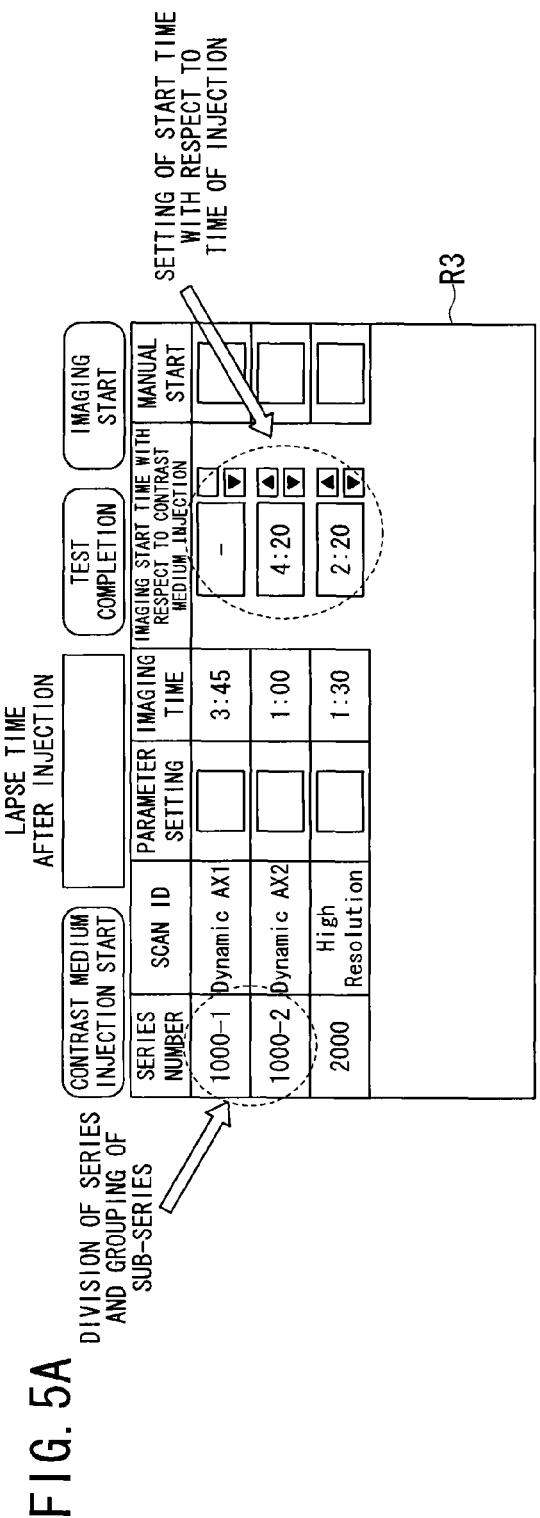
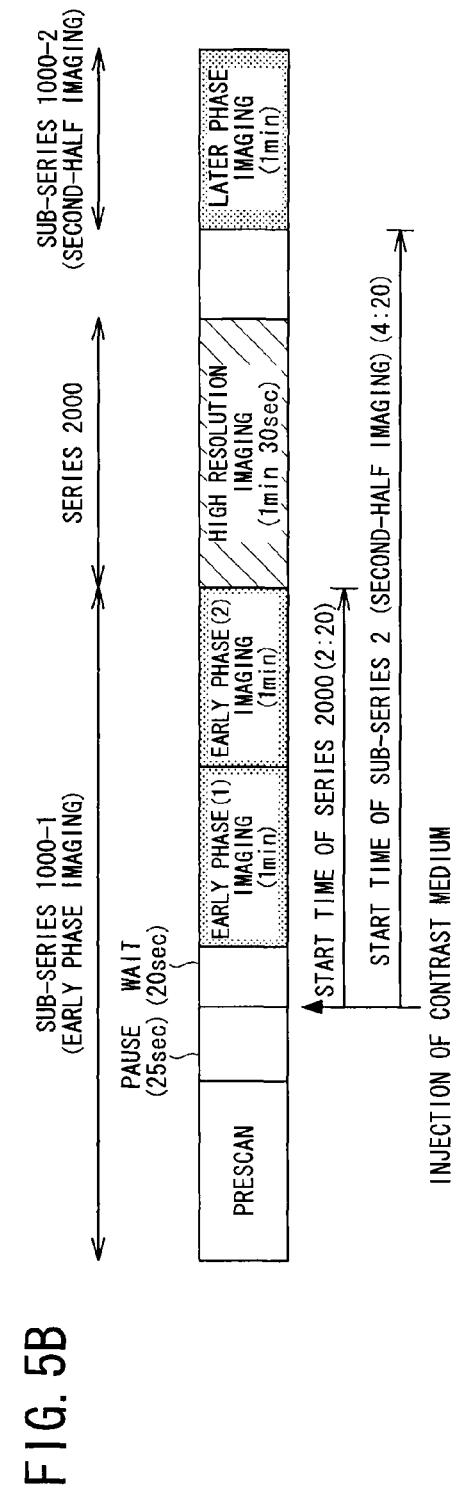
FIG. 5A
FIG. 5B

FIG. 7A

| CONTRAST MEDIUM INJECTION START | | LAPSE TIME AFTER INJECTION | | | | TEST COMPLETION | IMAGING START |
|---|---|---|---|---|---|---|---|
| SERIES NUMBER | SCAN ID | PARAMETER SETTING | IMAGING TIME | IMAGING START TIME WITH RESPECT TO CONTRAST MEDIUM INJECTION | | | MANUAL START |
| 1000-1 | Dynamic AX1 | ✓ | 2:20 | — | | | |
| 1000-2 | Dynamic AX2 | | 1:00 | 4:20 | | | |
| 2000 | High Resolution | | 1:30 | 2:20 | | | |

SAME GROUP

MODIFY PARAMETERS

R3

FIG. 7B PARAMETERS OF SUB-SERIES 1000-1

Basic | Advance

| NUMBER OF SLICES | 20 | NUMBER OF PHASE ENCODINGS | 256 |
| THICKNESS OF SLICES | 6.00 | PHASE ENCODING DIRECTION | Y |
| SLICE CENTER OFFSET | 200.0 | PI reduction factor | 1.5 |
| SLICE DIRECTION | AXIAL | NUMBER OF INTEGRATIONS | 2.0 |

R4

AUTOMATICALLY REFLECT MODIFICATION OF PARAMETER (128→256)

FIG. 7C PARAMETERS OF SUB-SERIES 1000-2

Basic | Advance

| NUMBER OF SLICES | 20 | NUMBER OF PHASE ENCODINGS | 256 |
| THICKNESS OF SLICES | 6.00 | PHASE ENCODING DIRECTION | Y |
| SLICE CENTER OFFSET | 200.0 | PI reduction factor | 1.5 |
| SLICE DIRECTION | AXIAL | NUMBER OF INTEGRATIONS | 2.0 |

| SERIES NUMBER | SCAN ID | PARAMETER SETTING | IMAGING TIME | IMAGING START TIME WITH RESPECT TO CONTRAST MEDIUM INJECTION | |
|---|---|---|---|---|---|
| 1000-1 | Dynamic AX1 | ☐ | 3:45 | — | ◀ ▶ |
| 1000-2 | Dynamic AX2 | ☐ | 1:00 | 1:20 | ◀ ▶ |
| 2000 | High Resolution | ☐ | 1:30 | 2:20 | ◀ ▶ |
| 1000-3 | Dynamic AX3 | ☐ | 1:00 | 4:20 | ◀ ▶ |

CONTRAST MEDIUM INJECTION START — LAPSE TIME AFTER INJECTION — TEST COMPLETION — IMAGING START — MANUAL START

DIVISION OF SERIES AND GROUPING OF SUB-SERIES

IMAGING START TIME OF SUB-SERIES 1000-2 :
4:20 AS PLANNED   4:22 IN ACTUALITY

IMAGING START TIME OF SERIES 2000 :
2:20 AS PLANNED   2:14 IN ACTUALITY

TEST INFORMATION : PATIENT C

| OTHER REGISTERED PATIENTS | LAPSE TIME AFTER INJECTION | IMAGING START TIME (LIMIT) |
|---|---|---|
| PATIENT A | 15:20 | 22:00 |
| PATIENT B | 8:15 | 22:00 |

LAPSE TIME AFTER INJECTION: 0:20

| SERIES NUMBER | SCAN ID | PARAMETER SETTING | IMAGING TIME | IMAGING START TIME WITH RESPECT TO CONTRAST MEDIUM INJECTION |
|---|---|---|---|---|
| 1000 | FIRST-HALF IMAGING | ☐ | 3:00 | 22:00 |
| 2000 | SECOND-HALF IMAGING | ☐ | 4:00 | 22:00 |

CONTRAST MEDIUM INJECTION START | TEST COMPLETION | IMAGING START

TIME (3)

FIG. 19B

TEST INFORMATION : PATIENT A

| OTHER REGISTERED PATIENTS | LAPSE TIME AFTER INJECTION | IMAGING START TIME (LIMIT) |
|---|---|---|
| PATIENT B | 19:30 | 22:00 |
| PATIENT C | 9:05 | 22:00 |

LAPSE TIME AFTER INJECTION: 23:05

| SERIES NUMBER | SCAN ID | PARAMETER SETTING | IMAGING TIME | IMAGING START TIME WITH RESPECT TO CONTRAST MEDIUM INJECTION |
|---|---|---|---|---|
| 1000 | FIRST-HALF IMAGING | ☐ | 3:00 | |
| 2000 | SECOND-HALF IMAGING | ☐ | 4:00 | 22:00 |

CONTRAST MEDIUM INJECTION START | TEST COMPLETION | IMAGING START

TIME (4)

FIG. 22

MAGNETIC RESONANCE IMAGING APPARATUS

CROSS-REFERENCE TO RELATED APPLICATIONS

This application is based upon and claims the benefit of priority from Japanese Patent Applications No. 2012-31047 filed on Feb. 15, 2012, the entire contents of which are incorporated herein by reference.

FIELD

An embodiment of the present invention relates to a magnetic resonance imaging apparatus.

BACKGROUND

A magnetic resonance imaging apparatus is an imaging apparatus that excites a nuclear spin in an object placed in a static magnetic field with a radio frequency (RF) signal at a Larmor frequency and reconstruct an image from a magnetic resonance signal produced by the object in response to the excitation.

In the magnetic resonance imaging, there is a field of diagnosis that involves injecting a contrast medium into an object and imaging the process of absorption of the contrast medium into an affected part, such as a tumor, through the blood vascular system with the lapse of time, such as in an early phase and a later phase. The imaging of this type is referred to as dynamic imaging using a contrast medium. A gadolinium contrast medium or the like is used in a conventional dynamic imaging performed by a magnetic resonance imaging apparatus.

In the diagnostic imaging of liver or the like, in addition to the dynamic imaging using a contrast medium that is to be absorbed through the blood vascular system described above, an imaging method using a newly developed contrast medium (such as the contrast medium referred to as Primovist) that is absorbed by the liver cells themselves has become popular in recent years.

In the dynamic imaging described above, a series of imagings are performed at a plurality of times, such as before injection of the contrast medium and the early phase and the later phase after injection of the contrast medium. The series of imagings is referred to as a "series" herein. In one imaging series, imagings are performed under basically the same imaging conditions except that the imagings are performed at different points in time, such as before injection of the contrast medium, in the early phase and in the later phase. The imaging conditions include the part to be imaged, the number of imaging slices, the positions of the imaging slices, the resolution, and specifications including a parameter of a pulse sequence closely related to these imaging conditions.

In a dynamic imaging series, the imaging before injection of the contrast medium and the imaging in the early phase are successively performed each in about 1 minute. However, a certain length of time has to be waited until the contrast medium is absorbed in the affected part, such as a tumor, before starting the imaging in the later phase. Therefore, an idle time of 2 to 3 minutes or so occurs between the imaging in the early phase and the imaging in the later phase. During the idle time, the patient has to stay lying on the bed and wait for the subsequent imaging.

On the other hand, in testing of one patient using the contrast medium, another imaging series is often performed in succession in addition to the dynamic imaging described above. For example, an imaging series with higher resolution may be performed after the dynamic imaging series is performed.

In such a case, if the whole or part of the another imaging series that would otherwise be performed after the dynamic imaging series can be performed in the idle time of the dynamic imaging series, the total imaging time of the patient can be reduced, and the burden on the patient can be reduced.

However, the conventional magnetic resonance imaging apparatus performs time management and imaging condition management separately for each series and therefore cannot perform imaging by inserting an imaging series into another imaging series.

In diagnosis of a liver cell using a contrast medium, such as Primovist described above, a waiting time of about 20 minutes is required after injection of the contrast medium for Primovist to be absorbed in the liver cell. According to the conventional technique, the patient has to stay on the bed and wait for the 20 minutes to pass. The time of 20 minutes is long enough to change patients and complete the whole or part of the imaging of another patient, thereby reducing the burden on the patients staying and waiting on the bed and the total imaging time of the patients.

However, the conventional magnetic resonance imaging apparatus performs time management and imaging condition management separately for each patient and therefore cannot insert an imaging of another patient into the imaging of one patient to perform the imaging of the another patient before the whole of the imaging of the one patient is completed. If the imaging is performed by changing patients, the imaging technician has to manage the time after injection of the contrast medium for each patient with a stopwatch or the like on his own, for example.

In view of such circumstances, in order to enable efficient use of the idle time of the contrast medium imaging, there is a demand for a magnetic resonance imaging apparatus that can perform time management and imaging condition management for combining a plurality of series of imagings or imagings of a plurality of patients.

SUMMARY

A magnetic resonance imaging apparatus according to an embodiment is a magnetic resonance imaging apparatus that performs a contrast medium imaging, comprising: a time management part that measures and manages a lapse time after injection of a contrast medium; a setting part that sets a start time of a second-half imaging in the form of a lapse time after injection of contrast medium, the second-half imaging being performed a predetermined idle time after a first-half imaging and the first-half imaging being performed after injection of the contrast medium; and a display part that displays at least the lapse time measured by the time management part and the start time set by the setting part.

A magnetic resonance imaging apparatus according to another embodiment is a magnetic resonance imaging apparatus that performs a contrast medium imaging, comprising: a series dividing part that divides a first series including an early phase imaging performed after injection of a contrast medium, a predetermined idle time provided after the early phase imaging and a later phase imaging performed after the idle time into a second series including the early phase imaging and a third series including the later phase imaging; and a control part that controls an imaging start time of the second series and an imaging start time of the third series.

BRIEF DESCRIPTION OF DRAWINGS

FIGS. 5A and 5B are diagrams for illustrating an example of division of an imaging series and insertion of another imaging series;

FIGS. 7A-7C are conceptual diagrams for illustrating a method of managing sub-series resulting from the division as one group and reflecting an imaging condition (parameter) of one of the sub-series in the group in an imaging condition of another sub-series;

FIG. 9 is a diagram showing an example of the display screen in a case where one imaging series is divided into three sub-series;

FIG. 16 is a diagram for illustrating a content displayed on the screen in a multiple patient composite imaging (before start of the imaging);

FIGS. 19A and 19B are diagrams showing examples of the display on the screen at a time (3) and a time (4) in FIG. 17;

FIG. 22 is a diagram for illustrating an example of a display of the time available for changing patients.

DESCRIPTION OF EMBODIMENTS

In the following, embodiments of the present invention will be described with reference to the accompanying drawings.

(1) Configuration

Figure 1:
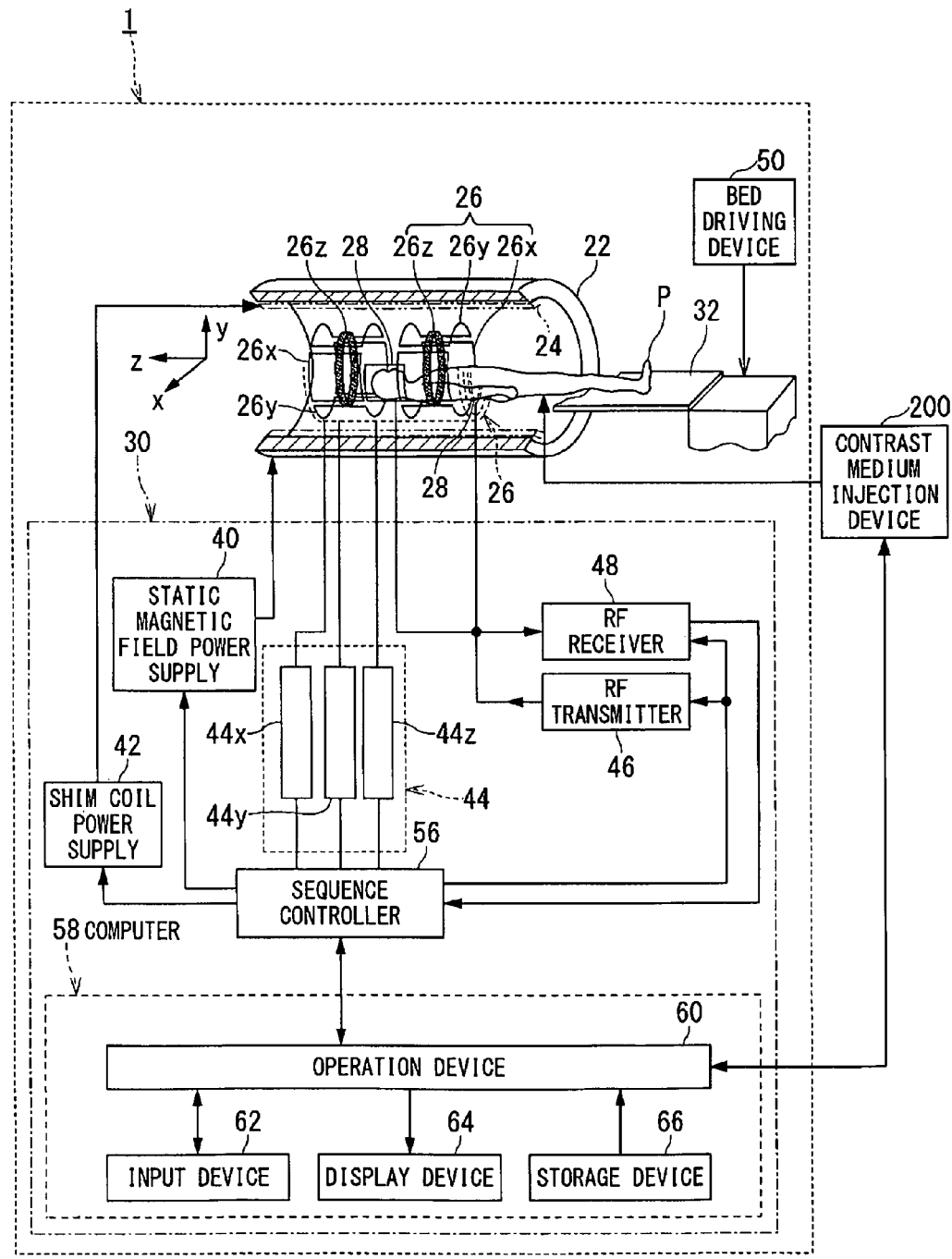
FIG. 1 is a diagram showing an example of a configuration of the whole of a magnetic resonance imaging apparatus.

FIG. 1 is a block diagram showing a configuration of the whole of a magnetic resonance imaging apparatus 1 according to this embodiment. As shown in FIG. 1, the magnetic resonance imaging apparatus 1 includes a cylindrical static magnetic field magnet 22 that produces a static magnetic field, a cylindrical shim coil 24 provided in the static magnetic field magnet 22 with an axis thereof aligned with an axis of the static magnetic field magnet 22, a gradient magnetic field coil 26, a transmitting or receiving RF coil 28, a control system 30 and a bed 32 on which an object (patient) P is to be placed, for example. Furthermore, the control system 30 includes a static magnetic field power supply 40, a shim coil power supply 42, a gradient magnetic field power supply 44, an RF transmitter 46, an RF receiver 48, a bed driving device 50, a sequence controller 56 and a computer 58, for example. Furthermore, the computer 58 includes an operation device 60, an input device 62, a display device 64 and a storage device 66, for example, as internal components thereof.

The static magnetic field magnet 22 is connected to the static magnetic field power supply 40 and produces a static magnetic field in an imaging space according to a current supplied from the static magnetic field power supply 40. The shim coil 24 is connected to the shim coil power supply 42 and makes the static magnetic field uniform according to a current supplied from the shim coil power supply 42. The static magnetic field magnet 22, which is often formed by a superconducting coil, is connected to, and receives a current from, the static magnetic field power supply 40 when the magnet 22 is to be excited and is typically disconnected once the magnet 22 is excited. As an alternative, the static magnetic field magnet 22 may be a permanent magnet, and the static magnetic field power supply 40 may be omitted.

The gradient magnetic field power supply 44 includes an X-axis gradient magnetic field power supply 44$x$, a Y-axis gradient magnetic field power supply 44$y$ and a Z-axis gradient magnetic field power supply 44$z$. Note that, in FIG. 1, an axial direction of the static magnetic field magnet 22 and the shim coil 24 is a Z-axis direction, a vertical direction is a Y-axis direction, and a direction perpendicular to these two directions is an X-axis direction.

The gradient magnetic field coil 26 includes an X-axis gradient magnetic field coil 26$x$, a Y-axis gradient magnetic field coil 26$y$ and a Z-axis gradient magnetic field coil 26$z$, which are arranged in a cylindrical configuration in the static magnetic field magnet 22. The X-axis gradient magnetic field coil 26$x$, the Y-axis gradient magnetic field coil 26$y$ and the Z-axis gradient magnetic field coil 26$z$ are connected to the X-axis gradient magnetic field power supply 44$x$, the Y-axis gradient magnetic field power supply 44$y$ and the Z-axis gradient magnetic field power supply 44$z$, respectively.

According to currents supplied from the gradient magnetic field power supplies 44$x$, 44$y$ and 44$z$, the gradient magnetic field coils 26$x$, 26$y$ and 26$z$ produce gradient magnetic fields Gx, Gy and Gz in the X-axis, Y-axis and Z-axis directions in the imaging space, respectively.

The gradient magnetic fields Gx, Gy and Gz in the three axial directions of the apparatus coordinate system can be combined to arbitrarily set directions of a gradient magnetic field Gss in a slice direction, a gradient magnetic field Gpe in a phase encoding direction and a gradient magnetic field Gro in a readout direction (frequency encoding direction), which are logical axes. The gradient magnetic fields in the slice direction, the phase encoding direction and the readout direction are superposed on the static magnetic field.

The RF transmitter 46 generates an RF pulse at a Larmor frequency that causes a nuclear magnetic resonance based on control information input from the sequence controller 56 and transmits the RF pulse to the transmitting RF coil 28. The RF coil 28 may be a transmitting whole body coil (WBC) that transmits an RF pulse and receives a magnetic resonance signal (MR signal) from the object, or a receive-only coil provided in the vicinity of the bed 32 or the object P (referred to also as a local coil).

The MR signal received by the RF coil 28 is fed to the RF receiver 48 through a signal cable.

The RF receiver 48 generates raw data, which is digital complex data, by performing various signal processings, such as pre-amplification, intermediate frequency conversion, phase detection, low frequency amplification and filtering, on the received MR signal and then performing analog to digital (A/D) conversion on the processed received MR signal. The RF receiver 48 inputs the raw data generated from the MR signal to the sequence controller 56.

The sequence controller 56 causes generation of the gradient magnetic fields Gx, Gy and Gz and the RF pulse that satisfy an imaging condition including a set pulse sequence under the control of the operation device 60 of the computer 58. Furthermore, the sequence controller 56 receives an MR signal responsive to the gradient magnetic fields Gx, Gy and Gz and the RF pulse as raw data from the RF receiver 48 and outputs the MR signal to the operation device 60.

The operation device 60 includes a processor, for example. The operation device 60 generates image data on the object by performing a reconstruction processing or various image processings including inverse Fourier transform on the raw data input from the sequence controller 56. The generated image data is displayed on the display device 64.

Furthermore, the operation device 60 performs setting or modification of the imaging condition including various pulse sequences or setting or modification of time management information used in contrast medium imaging based on various setting information input to the input device 62 by a user operation, and controls the sequence controller 56 based on the set or modified imaging condition or time management information. To the operation device 60, a control signal from a contrast medium injection device 200, which is separately provided, is connected.

Figure 2:
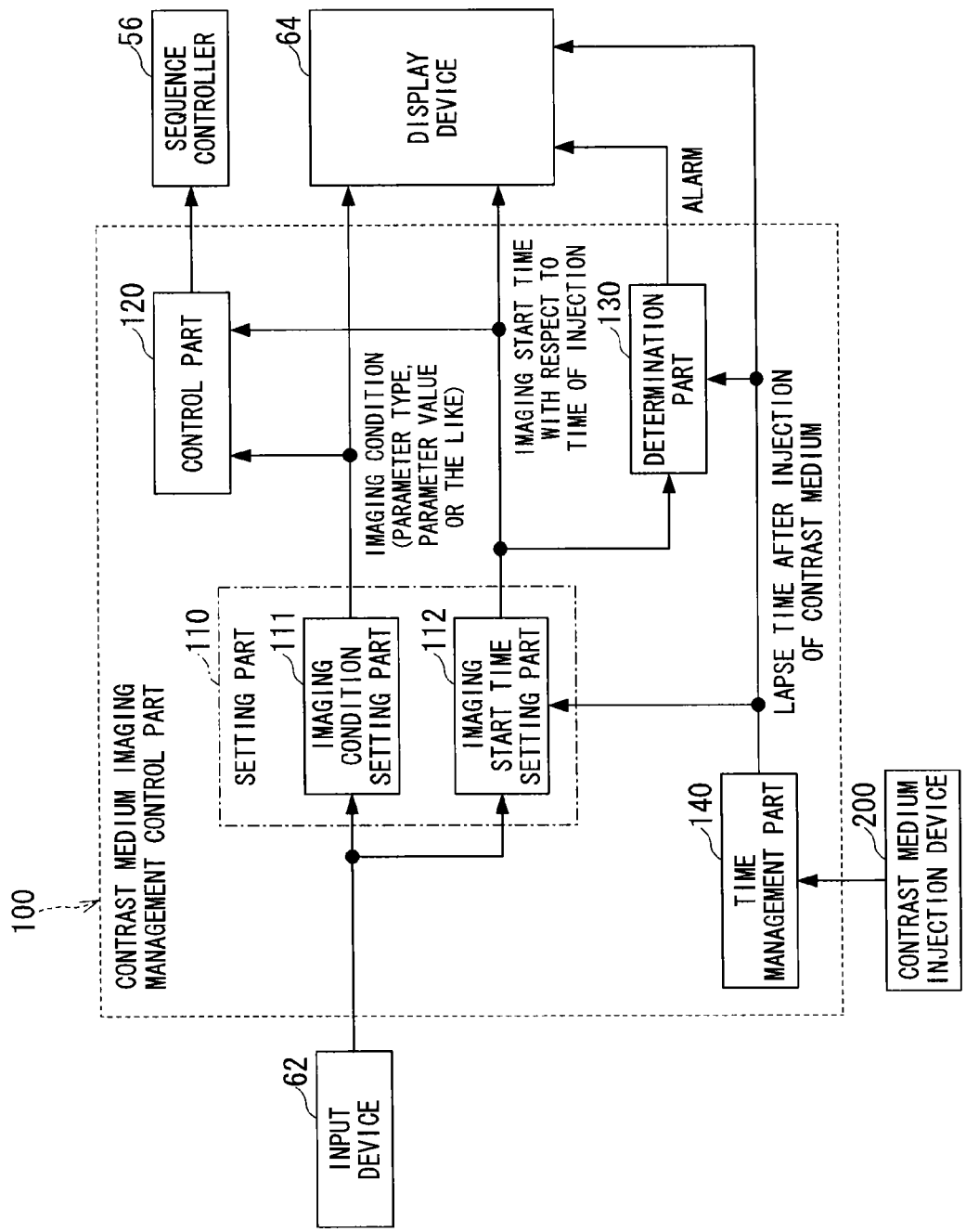
FIG. 2 is a functional block diagram showing a contrast medium imaging management control part implemented by an operation device according to an embodiment.

FIG. 2 is a diagram showing an example of a configuration of functional blocks of a contrast medium imaging management control part 100 implemented by the operation device 60 according to this embodiment. The functions of the functional blocks shown in FIG. 2 may be implemented by a program code stored in the storage device 66 executed by the processor of the operation device 60 or by hardware, such as ASIC.

The contrast medium imaging management control part 100 according to this embodiment includes a setting part 110 including an imaging condition setting part 111 and an imaging start time setting part 112, a control part 120, a determination part 130 and a time management part 140, for example.

The imaging condition setting part 111 sets various imaging conditions including a pulse sequence based on information input from the input device 62. The imaging start time setting part 112 sets, as a lapse time after injection of the contrast medium, a start time of a second-half imaging, which is performed a predetermined idle time after a first-half imaging, which is performed immediately after injection of the contrast medium. The time management part 140 measures and manages the lapse time after injection of the contrast medium.

The control part 120 controls the sequence controller 56 to start the second-half imaging based on the lapse time measured by the time management part 140 and the start time set by the imaging start time setting part 112. Furthermore, the control part 120 controls the sequence controller 56 based on the various imaging conditions set by the imaging condition setting part 111.

The determination part 130 determines the validity of the imaging conditions set by the imaging condition setting part 111, the start time set by the imaging start time setting part 112 or the like and produces an alarm display on the display device 64 if the set values conflict with each other or are hardly feasible. For example, in a case where "another imaging" is to be additionally performed during the idle time between the first-half imaging and the second-half imaging, if the imaging time of the "another imaging" is longer than the idle time, the determination part 130 determines in the planning phase that the "another imaging" is not feasible and outputs alarm information indicative of that determination to the display device 64. Even during imaging, if the second-half imaging is expected to fail to start at the set start time because of the "another imaging" inserted in the idle time, the determination part 130 makes the same determination and outputs the alarm information indicative of that determination to the display device 64.

(2) Operation of Contrast Medium Imaging Management Control Part

As described above, in a case where dynamic imaging is performed by injecting a gadolinium-based contrast medium to a patient, an early phase imaging (first-half imaging) that involves a plurality of (two, for example) imagings performed in a relatively early phase after injection of the contrast medium and a later phase imaging (second-half imaging) that involves an imaging performed a predetermined time after the injection of the contrast medium are performed. There is a waiting time (idle time) of typically 2 to 3 minutes or so between the early phase imaging and the later phase imaging. This embodiment provides a method of inserting "another imaging" planned to be performed on the same patient, such as another imaging of higher resolution than the dynamic imaging, into the idle time of the dynamic imaging, and performing the dynamic imaging and the "another imaging" with high efficiency and reliability. This imaging method will be referred to as a "single patient composite imaging", hereinafter.

On the other hand, in imaging for diagnosis of a liver cell using a recently developed Primovist-based contrast medium, a long waiting time (idle time) of about 20 minutes is required after injection of the contrast medium for Primovist to be absorbed in the liver cell. The time of 20 minutes is long enough to change patients and complete the whole or part of imaging of another patient. In the imaging using the Primovist-based contrast medium, it is typical that the dynamic imaging described above is performed in a relatively early phase after injection of the contrast medium, and a hepatocyte phase imaging is then performed after a waiting time of about 20 minutes, which is required for the contrast medium to be absorbed in the liver cell. The idle time of 20 minutes is long enough to change patients and perform imaging of another patient. Thus, this embodiment also provides a method of changing patients during the idle time between the dynamic imaging and the hepatocyte phase imaging and performing contrast imaging of a plurality of patients with high efficiency and reliability. This imaging method will be referred to as a "multiple patient composite imaging", hereinafter.

In the following, the single patient composite imaging and the multiple patient composite imaging will be separately described.

(3) Single Patient Composite Imaging

In the following description of the single patient composite imaging according to this embodiment, a setting phase in which an imaging condition for the imaging is set and an execution phase in which the imaging is performed will be separately described.

In the setting phase of the single patient composite imaging, a processing is performed to divide a dynamic imaging series and insert "another imaging" series in the idle time of the dynamic imaging. In addition, a processing of grouping the sub-series resulting from the division of the dynamic imaging series is also performed.

Figure 3A:
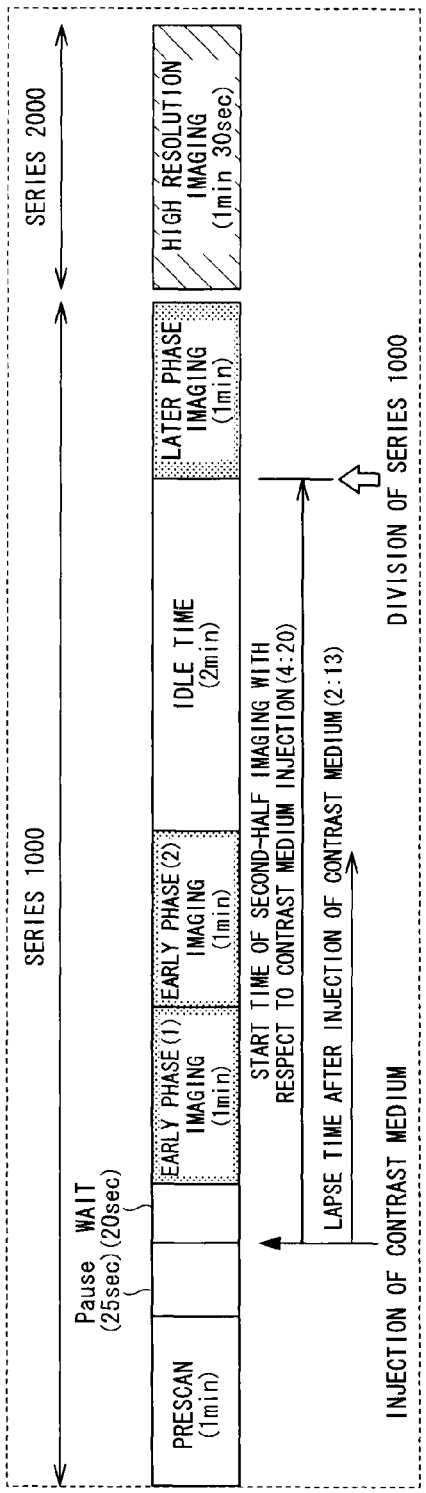
FIGS. 3A and 3B are diagrams showing an example of a dynamic imaging series yet to be divided and another imaging series yet to be inserted in an idle time.

FIG. 3A is a diagram showing an example of a dynamic imaging series (series 1000) yet to be divided and another imaging series (series 2000) yet to be inserted in the idle time.

In the dynamic imaging, one minute of prescan is performed before injection of the contrast medium, and then, 25 seconds after completion of the prescan, the contrast medium is injected. Then, 20 seconds after injection of the contrast medium, one minute of early phase (1) imaging and one minute of early phase (2) imaging are performed. Then, there is provided an idle time of 2 minutes, and one minute of later phase imaging is performed after the idle time. Before division, this series of imagings is set as one series (series 1000). In the single patient composite imaging, the early phase (1) imaging and the early phase (2) imaging that are performed before the idle time are collectively referred to as a first-half imaging, and the later phase imaging that is performed after the idle time is referred to as a second-half imaging.

The series 2000 is another imaging series planned to be performed on the same patient. In this example, the series 2000 is specified as a high resolution imaging whose resolution is higher than that of the series 1000.

According to the conventional imaging method, the series 1000 is first performed, and the series 2000 of high resolution imaging is performed after completion of the later phase imaging of the series 1000. As for the start timing of each series, in a case where the imaging start procedure is set to be "manual", the imaging series 1000 is manually started, and then, the imaging series 2000 is manually started after the user ascertains the completion of the series 1000. On the other hand, in a case where the imaging start procedure is set to be "automatic", although the imaging series 1000 is manually stated, the imaging series 2000 is automatically started immediately after completion of the imaging series 1000. In any case, however, no imaging occurs during the idle time of the series 1000, and the patient has to stay and wait on the bed during the idle time.

By contrast, in the single patient composite imaging according to this embodiment, a processing is performed to divide the series 1000 and insert the series 2000 in the idle time of the series 1000. As a result, there is effectively no idle time, and the total imaging time can be reduced.

Figure 3B:
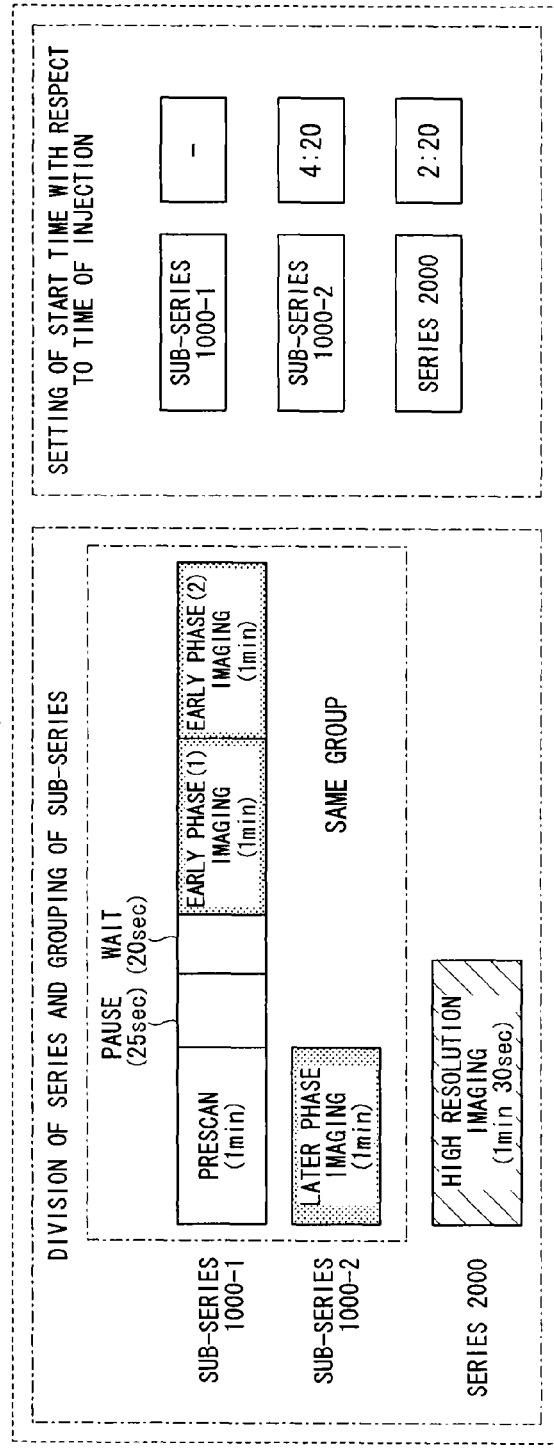

FIG. 3B shows a first-half imaging sub-series (series 1000-1) and a second-half imaging sub-series (series 1000-2) resulting from the division of the series 1000. FIG. 3B also shows the series 2000. The series 1000 can be divided in various manners. For example, according to a possible method, the arrangement of the series 1000 shown in FIG. 3A is displayed on a part of the display device 64, and a region (region corresponding to the idle time) between the early phase (2) imaging and the later phase imaging is pointed and clicked with a pointer device, such as a mouse, of the input device 62.

To insert the series 2000 in the idle time of the series 1000, it is enough that the imaging start time of the second-half imaging sub-series 1000-2 resulting from the division and the imaging start time of the series 2000 are set. In this process, if the start time of the series 2000 is set to be immediately after completion of the first-half imaging sub-series 1000-1 resulting from the division, and the imaging start time of the second-half imaging sub-series 1000-2 is set to be immediately after completion of the series 2000, the series 2000 can be inserted in the idle time of the series 1000 yet to be divided.

A more specific example of the method of dividing the series 1000 and inserting the series 2000 will be described with reference to a screen of the display device 64.

Figure 4:
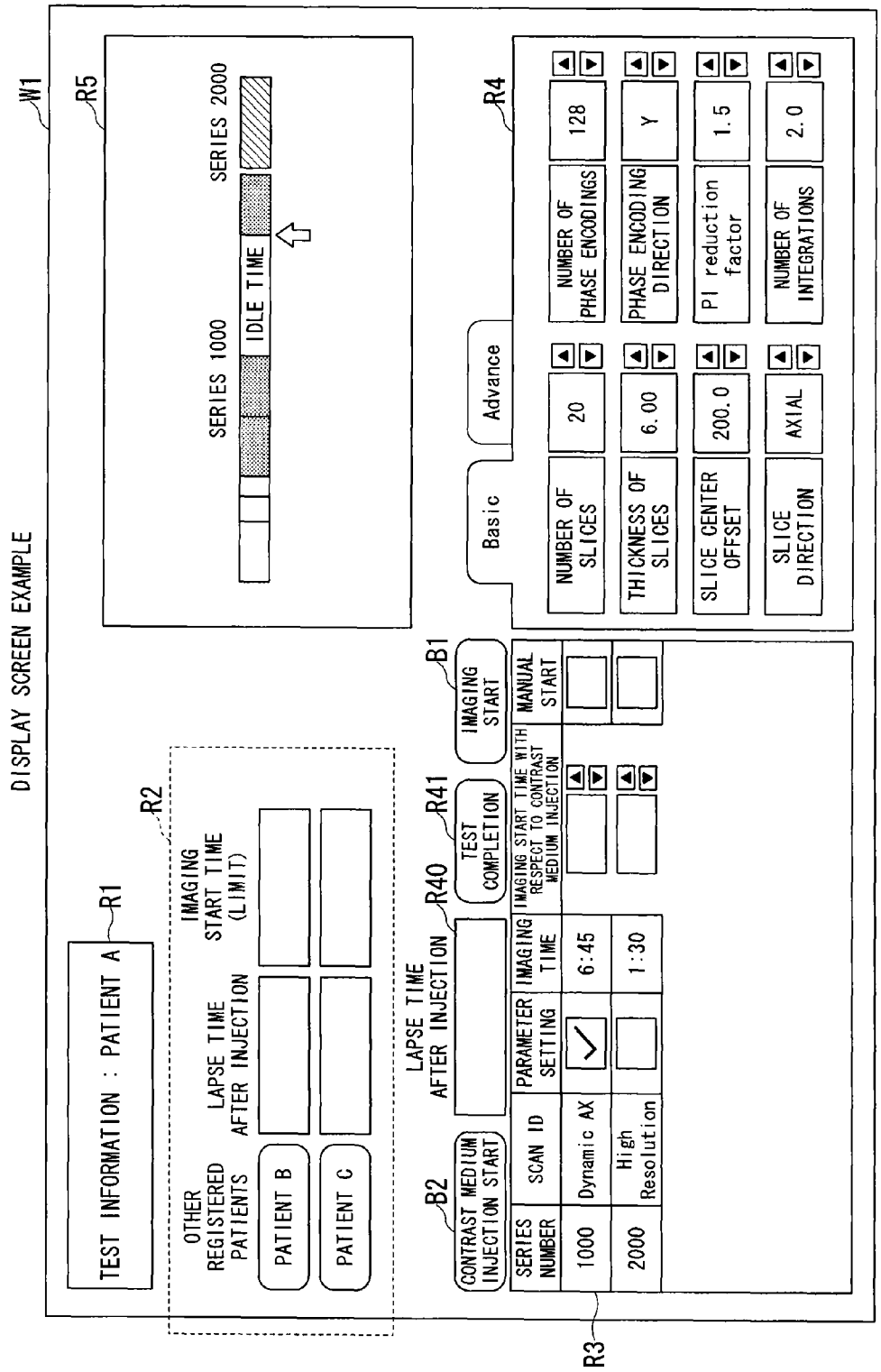
FIG. 4 is a diagram showing an example of a display on a screen of a display device.

FIG. 4 is a diagram showing an example of a display on a screen W1 of the display device 64. In an upper left area of the screen W1, a "test and patient identification information" region R1 is displayed for identification of a test yet to be performed or being performed and a patient A to be tested. A "waiting patient information" region R2 used in the multiple patient composite imaging is provided below the "test and patient identification information" region R1. The "waiting patient information" region R2 will be described later.

In a lower left area of the screen W1, a "series information" region R3 is provided in which information on a plurality of imaging series set for the patient to be tested (the patient A in this example) is displayed and set. In the example shown in FIG. 4, information on the series 1000 yet to be divided and the series 2000 is displayed in the "series information" region R3. The "series information" region R3 contains a "series number" field, a "SCAN ID" field, a "parameter setting" field, an "imaging time" field, a "imaging start time with respect to contrast medium injection" field and a "manual start" field arranged in the horizontal direction.

In the "series number" field and the "SCAN ID" field, the series number and the series identification name are displayed, respectively. The "parameter setting" field is used for selecting one of the plurality of series by clicking or other operations. The selected series is checkmarked. An imaging parameter of the selected series is displayed in a "parameter information" region R4 that is provided to the right of the "series information" region R3.

In the "imaging time" field in the "series information" region R3, the time required for each imaging series is displayed. The "imaging start time with respect to contrast medium injection" field is used for setting and displaying the imaging start time of each series with respect to the time of injection of the contrast medium. The "manual start" field is used for independently manually starting each series. If a box in the "manual start" field is clicked when the imaging start mode is set to be "manual", an imaging of the corresponding series is manually started. When the imaging start mode is set to be "automatic", any operation in the "manual start" field is invalid.

In a lower right area of the screen W1, the "parameter information" region R4 is provided, and an imaging parameter of the series selected by clicking or other operations in the "parameter setting" field is displayed in the "parameter information" region R4. The value of each imaging parameter is previously set and stored for each series by the imaging condition setting part 111 in the setting part 110, and the stored set values are displayed. Alternatively, a desired numeric value may be directly input to each box on the screen W1 through the input device 62, or the set value may be changed by using a "▲" button and a "▼" button.

Between the "waiting patient information" region R2 and the "series information" region R3, an "imaging start" button B1, a "contrast medium injection start" button B2, a "lapse time after injection" display field R40, a "test completion" display field R41 and the like are disposed.

When the imaging start mode is set to be "automatic", if the "imaging start" button B1 is clicked, the series set in the "series information" region R3 are automatically started in the order from top to bottom. However, if a start time is set in the "imaging start time with respect to contrast medium injection" field, the start time takes precedence. That is, when the "imaging start" button B1 is clicked, the imaging series whose start time is not set in the "imaging start time with respect to contrast medium injection" filed are started in the order from top to bottom, and any imaging series whose start time is set in the "imaging start time with respect to contrast medium injection" filed is started at the start time. When all the imaging series are completed, the "test completion" display field R41 is highlighted.

The "contrast medium injection start" button B2 is a button used for this apparatus to instruct the contrast medium injection device 200 (see FIG. 1) to inject the contrast medium. If the "contrast medium injection start" button B2 is clicked, the contrast medium injection device 200 starts injecting the contrast medium to the patient A, and the lapse time after the injection of the contrast medium to the patient A is displayed in the "lapse time after injection" display field R40. The lapse time is measured by the time management part 140 (see FIG. 2).

The contrast medium injection device 200 can also instruct to start injection of the contrast medium. In that case, the time information or timing signal indicative of the start of injection of the contrast medium is sent from the contrast medium injection device 200 to the apparatus 1, the time management part 140 measures the lapse time after the injection of the contrast medium based on the time information or timing signal, and the lapse time is displayed in the "lapse time after injection" display field R40 on the screen W1.

In an upper right area of the screen W1, a multipurpose display field R5 is provided. In the multipurpose display field R5, a scout image (an image used for determining or ascertaining the part to be imaged) of the patient A, information useful in various settings or the like is displayed. In the example shown in FIG. 4, a schematic graphic of the series 1000 yet to be divided and the series 2000 is displayed in order to facilitate division of the series 1000.

In division of the series 1000, as illustrated in the multipurpose display field R5, a pointer (arrow) is placed in the region between the early phase (2) imaging and the later phase imaging of the series 1000 (the region corresponding to the idle time) with the mouse or the like of the input device 62, and the mouse is clicked. The series 1000 can be divided by such a simple operation.

FIG. 5A shows an example of a display of the "series information" region R3 after the series 1000 is divided. The series 1000 is divided into the sub-series 1000-1 that corresponds to the first-half imaging and the sub-series 1000-2 that corresponds to the second-half imaging, and the imaging time of each sub-series is automatically displayed in the "imaging time" field (3 minutes and 45 seconds for the sub-series 1000-1 and 1 minute for the sub-series 1000-2). Note that the idle time of 2 minutes of the original series 1000 is automatically removed. The sub-series resulting from the division are recognized as belonging to the same group.

Once the division of the series is completed, the imaging start time of the series 2000 ("another imaging" performed on the patient A) and the imaging start time of the sub-series 1000-2 (second-half imaging) are set.

As shown in FIG. 5B, an imaging of the series 2000 can be inserted in the idle time of the series 1000 yet to be divided by setting the start time of the series 2000 to be immediately after completion of the first-half imaging sub-series 1000-1 resulting from the division and setting the imaging start time of the second-half imaging sub-series 1000-2 to be after completion of the series 2000.

Each imaging start time is not set with respect to the start time of the sub-series 1000-1 but set with respect to the time of injection of the contrast medium. As well known, in the contrast medium imaging, the timing of starting the second-half imaging after the time of injection of the contrast medium is essential. Thus, according to this embodiment, the start time of the imaging series is set with respect to the time of injection of the contrast medium.

In the example shown in FIGS. 5A and 5B, "2:20" (2 minutes and 20 seconds) is set in the "imaging start time with respect to contrast medium injection" field for the series 2000, and thus, the start time of the series 2000 is set to be immediately after the first-half imaging sub-series 1000-1 resulting from the division. On the other hand, "4:20" (4 minutes and 20 seconds) is set in the "imaging start time with respect to contrast medium injection" field for the sub-series 1000-2, and thus, the second-half imaging (the later phase imaging of the series 1000 yet to be divided) can be started 4 minutes and 20 seconds after the injection of the contrast medium. The lapse time of 4 minutes and 20 seconds is equal to the time between the injection of the contrast medium and the start of the later phase imaging in the originally planned dynamic imaging (series 1000) yet to be divided (see FIG. 3A).

Note that a graphic similar to that shown in FIG. 5B can also be displayed in the multipurpose display field R5 on the screen W1. That display allows the entire imaging sequence after the division and the insertion to be easily checked.

The processing of dividing a series and the processing of inserting another imaging described above are performed by the imaging start time setting part 112 in the setting part 110.

As described above, the magnetic resonance imaging apparatus 1 according to this embodiment can easily insert another imaging series in the idle time of a dynamic imaging series through a simple operation.

Figure 6A:
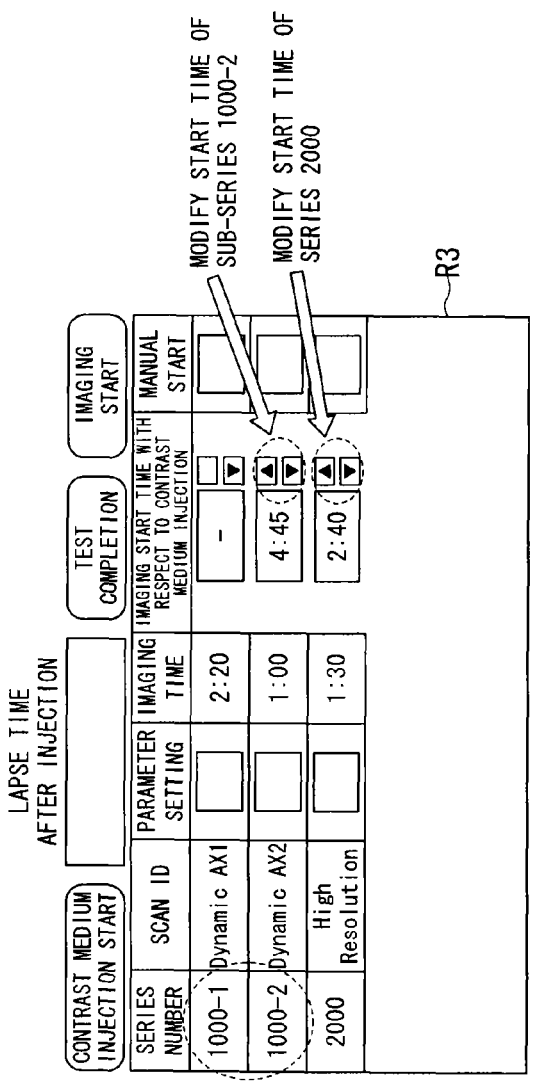
FIGS. 6A and 6B are diagrams for illustrating a method of modifying an imaging start time.
Figure 6B:
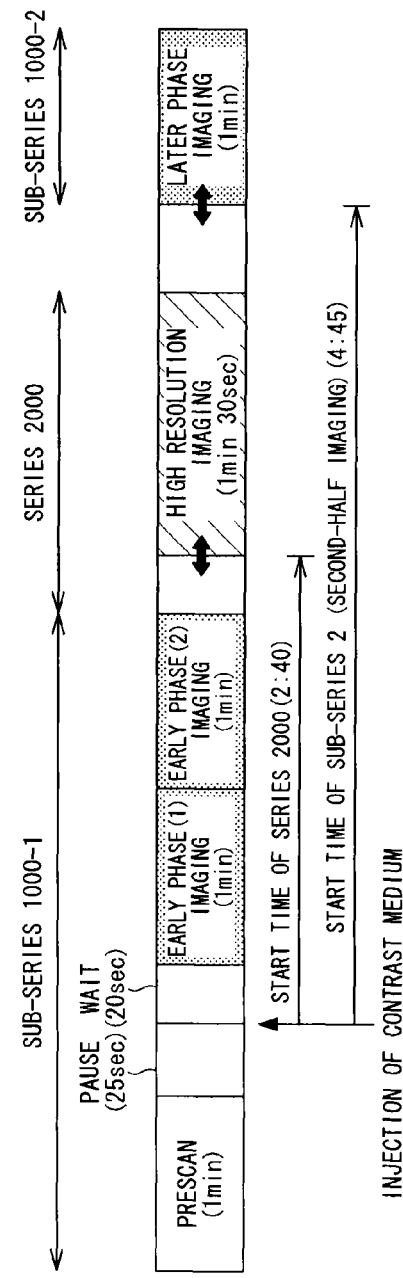

The imaging start time once set can be easily modified. In that case, for example, as shown in FIGS. 6A and 6B, the start time of the inserted series 2000 and the start time of the second-half imaging sub-series 1000-2 can be modified by clicking the "▲" button and the "▼" button in the "imaging start time with respect to contrast medium injection".

Furthermore, according to this embodiment, the imagings of the sub-series resulting from the division (the first-half imaging and the second-half imaging) are managed as one group, and if the imaging condition of any imaging in the group is modified, the modification to the imaging condition is automatically reflected in the imagings other than the imaging whose imaging condition is modified. As described above, in the dynamic imaging, the imagings are performed under basically the same imaging conditions in the early phase (1), in the early phase (2) and in the later phase, even if the imaging timings differ. Therefore, when a modification to the imaging condition of a sub-series resulting from the division occurs, if the modification is automatically reflected in the other imaging sub-series in the same group, the imaging conditions of the other imaging sub-series do not have to be modified separately, and therefore, the burden of operation is reduced.

FIGS. 7A to 7C are diagrams for illustrating this. For example, if the number of phase encodings of the sub-series 1000-1 is changed from "128" to "256" (FIGS. 7A and 7B), the number of phase encodings of the sub-series 1000-2 in the same group is also automatically changed from "128" to "256" (FIG. 7C).

Figures 8A, 8B:
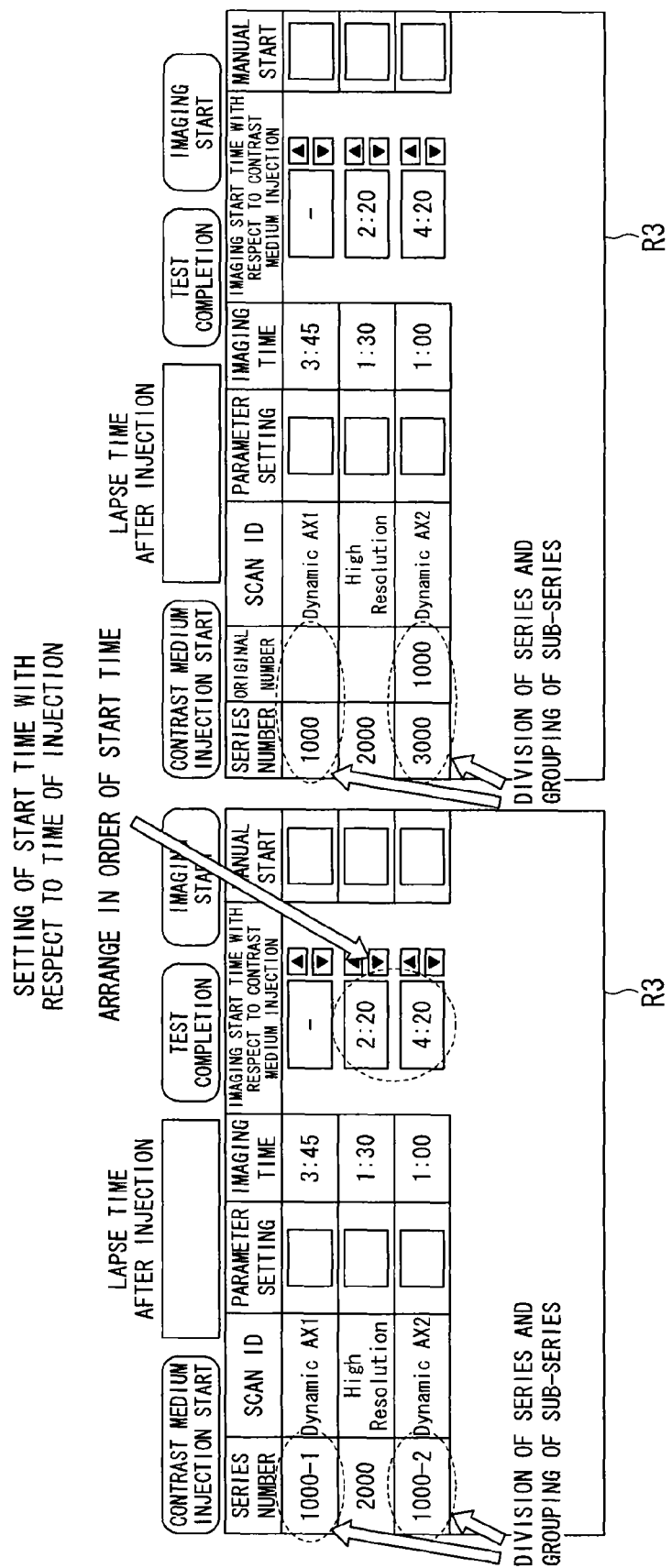
FIGS. 8A and 8B are diagrams showing another example of a display screen after an imaging series is divided.

FIGS. 8A and 8B to 10 are diagrams showing other examples of imaging sequence setting according to this embodiment. In the examples of the display of the "series information" region R3 shown in FIGS. 5A and 6A, the sub-series 1000-1, the sub-series 1000-2 and the series 2000 are displayed in this order. However, the order can be changed. As shown in FIG. 8A, the series and the sub-series can be rearranged in the "series information" region R3 in the order of the imaging start time set after the division.

Furthermore, the notation of the series numbers of the sub-series resulting from the division is not limited to the notation described above, such as 1000-1 and 1000-2, which is the original series number followed by a dash and a suffix number. For example, as illustrated in FIG. 8B, the series 1000 can be divided into a sub-series 1000 and a sub-series 3000, and the original series number of the sub-series 3000 can be displayed in an "original number" field in the "series information" region R3. Such a display can also allow the user to immediately recognize that the sub-series resulting from the division belong to the same group.

The number of sub-series resulting from division is not limited to 2 described above, and a series can be divided into three or more sub-series. FIG. 9 is a diagram showing an example of the display of the "series information" region R3 in a case where the series 1000 is divided into three sub-series 1000-1, 1000-2 and 1000-3. Such a display makes it obvious that one series has been divided into three sub-series and allows the fact that the sub-series resulting from the division belong to the same group to be easily recognized.

Figure 10:
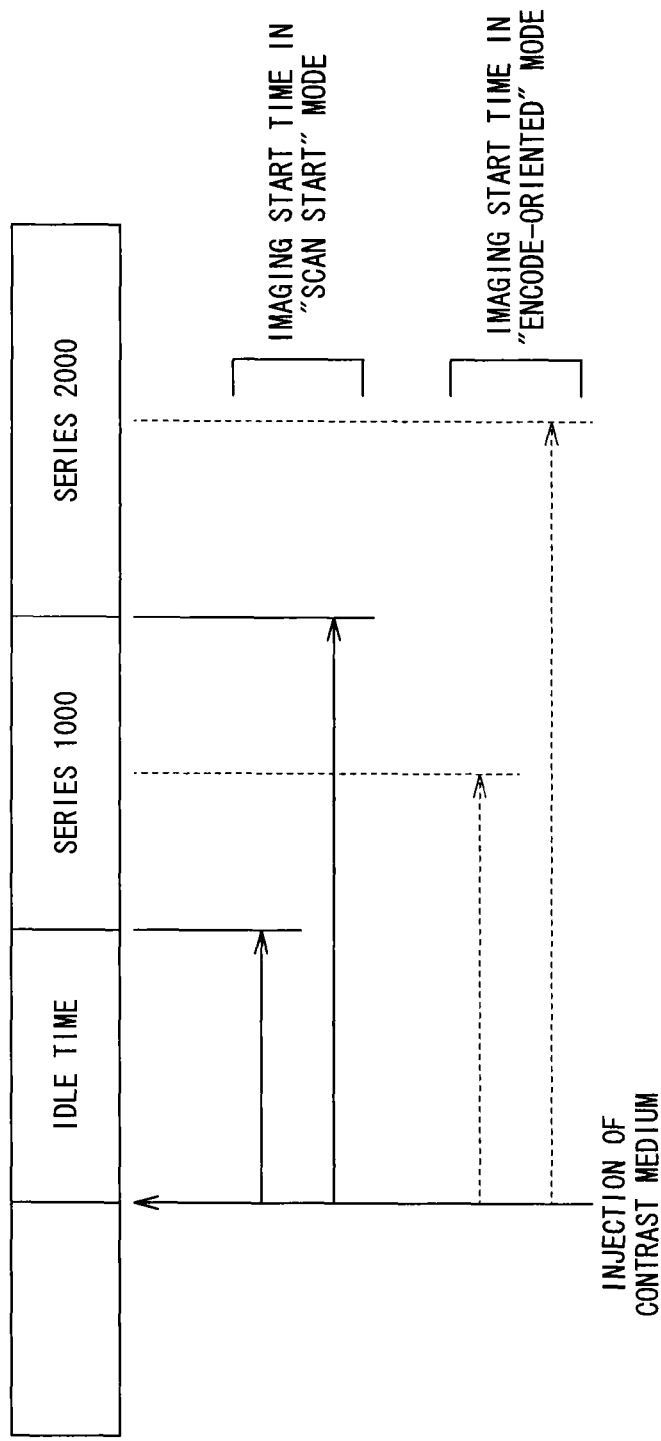
FIG. 10 is a conceptual diagram showing a mode of setting an imaging start time and the corresponding imaging start time.

As a further alternative, there may be a plurality of imaging start time setting modes so that the user can select a desired one from among the plurality of setting modes. For example, the imaging start time setting mode can be selected from among two imaging start time setting modes, a "Scan Start" mode and an "Encode-Oriented" mode. FIG. 10 is a diagram for illustrating these two imaging start time setting modes. In a case where the "Scan Start" mode is selected, the time from the time of injection of the contrast medium to the point of start of each series (the start point of the main scan excluding the prescan in the case where the imaging involves the prescan) is set as the imaging start time. On the other hand, in a case where the "Encode-Oriented" mode is selected, the time from the time of injection of the contrast medium to the central point of the phase encoding in each imaging series is set as the imaging start time.

When "another imaging" is to be inserted in the idle time of the dynamic imaging, "another imaging" having a longer imaging time than the idle time may be inserted by mistake. For example, as shown in FIG. 11, in a case where the start time of the series 2000, which is "another imaging", is set to be immediately after the first-half imaging (the start time is set at 2:20), and at the same time, the start time of the second-half imaging sub-series 1000-2 is set at 4:20, if the imaging time of the series 2000 is longer than the idle time (if the imaging time of the series 2000 is 2 minutes and 40 seconds, and the idle time is 2 minutes, for example), the "another imaging" cannot be inserted in actuality.

To avoid such a situation, the determination part 130 (see FIG. 2) according to this embodiment determines whether or not the imaging time of the "another imaging" to be inserted is longer than the idle time and instructs the display device 64 to display an alarm indication if the determination part 130 determines that the imaging time of the "another imaging" is longer than the idle time.

Figure 11:
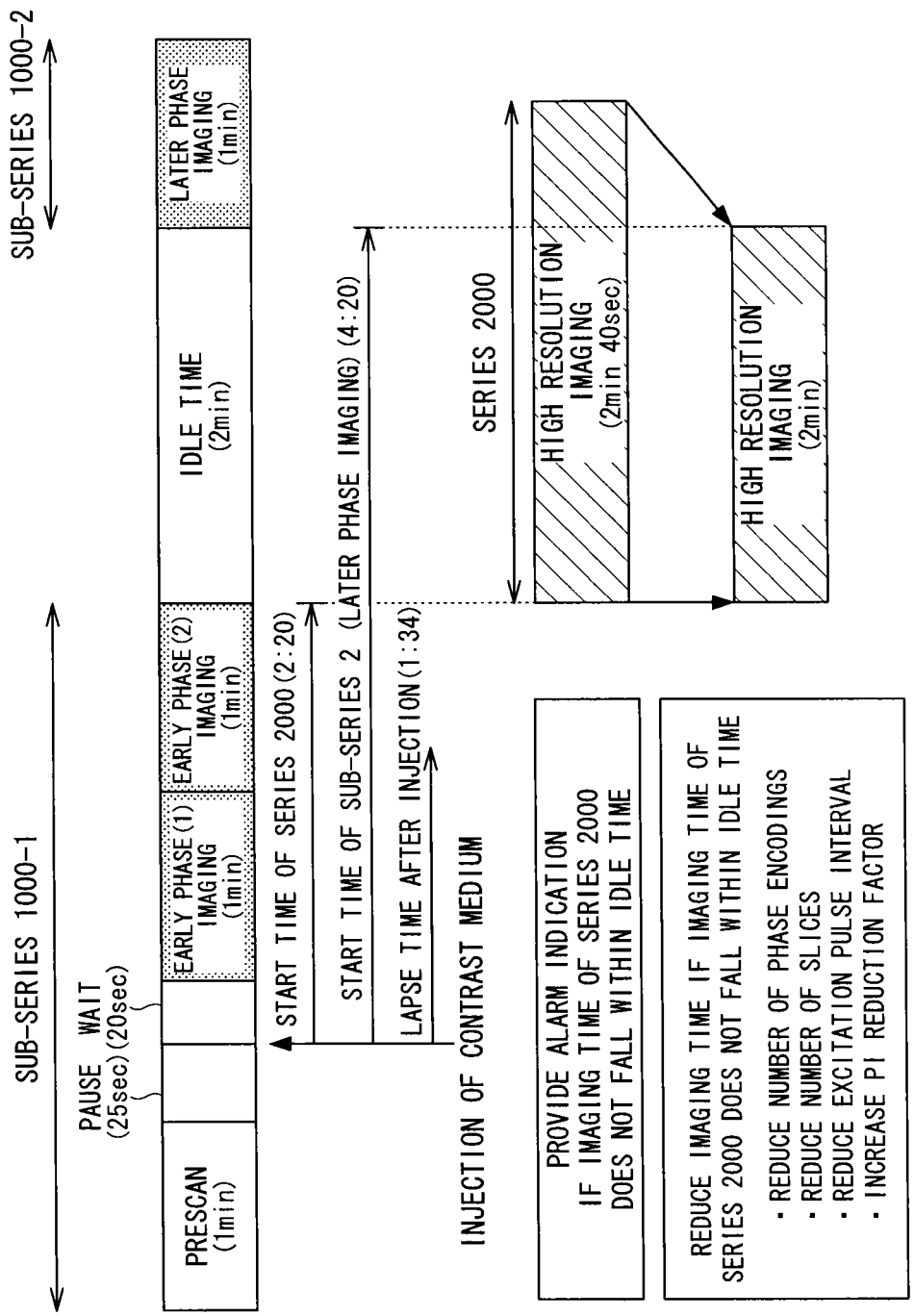
FIG. 11 is a conceptual diagram showing a method of providing an alarm or reducing an imaging time of an imaging to be inserted in an idle time in a case where the imaging time is longer than the idle time.

If the imaging time of the "another imaging" is longer than the idle time, a parameter value of the imaging condition of the "another imaging" may be automatically adjusted so that the imaging time of the "another imaging" is equal to or less than the idle time, before the alarm indication is displayed (see the lower part of FIG. 11). The automatic adjustment is performed by the imaging condition setting part 111 in the setting part 110.

In this process, the type of the parameter to be automatically adjusted is previously set, and the order of precedence among the types of the parameters to be adjusted is also previously determined. And the lower limit and the upper limit of the parameter value to be adjusted are also preferably previously set. Starting with the parameter type with the highest precedence, the imaging condition setting part 111 automatically adjusts the parameter value so that the imaging time of the "another imaging" falls within the idle time by gradually reducing the parameter value toward the lower limit thereof. The types of the parameters to be automatically adjusted include a parameter concerning the resolution, such as the number of phase encodings, a parameter concerning the size of the imaging region, such as FOV and the number of slices, the excitation pulse interval, and the reduction factor in the case where parallel imaging (PI) is performed, for example. With regard to the number of phase encodings, FOV, the number of slices, the excitation pulse interval and the like, the imaging time decreases as the parameter value decreases. With regard to the reduction factor of PI, the imaging time decreases as the parameter value increases.

If the imaging time of the "another imaging" does not become equal to or less than the idle time even after all the parameter values of the parameter types are reduced to their respective lower limits, an alarm indication can be displayed on the display device 64.

A magnetic resonance imaging apparatus according to another embodiment may include a series dividing part that divides a first series including an early phase imaging performed after injection of a contrast medium, a predetermined idle time provided after the early phase imaging and a later phase imaging performed after the idle time into a second series including the early phase imaging and a third series including the later phase imaging, and a control part that controls the imaging start time of the second series and the imaging start time of the third series.

A setting phase in which an imaging condition or an imaging sequence of the single patient composite imaging is set has been described above. In the following, an execution phase in which the single patient composite imaging is performed will be described.

Figures 12A, 12B:
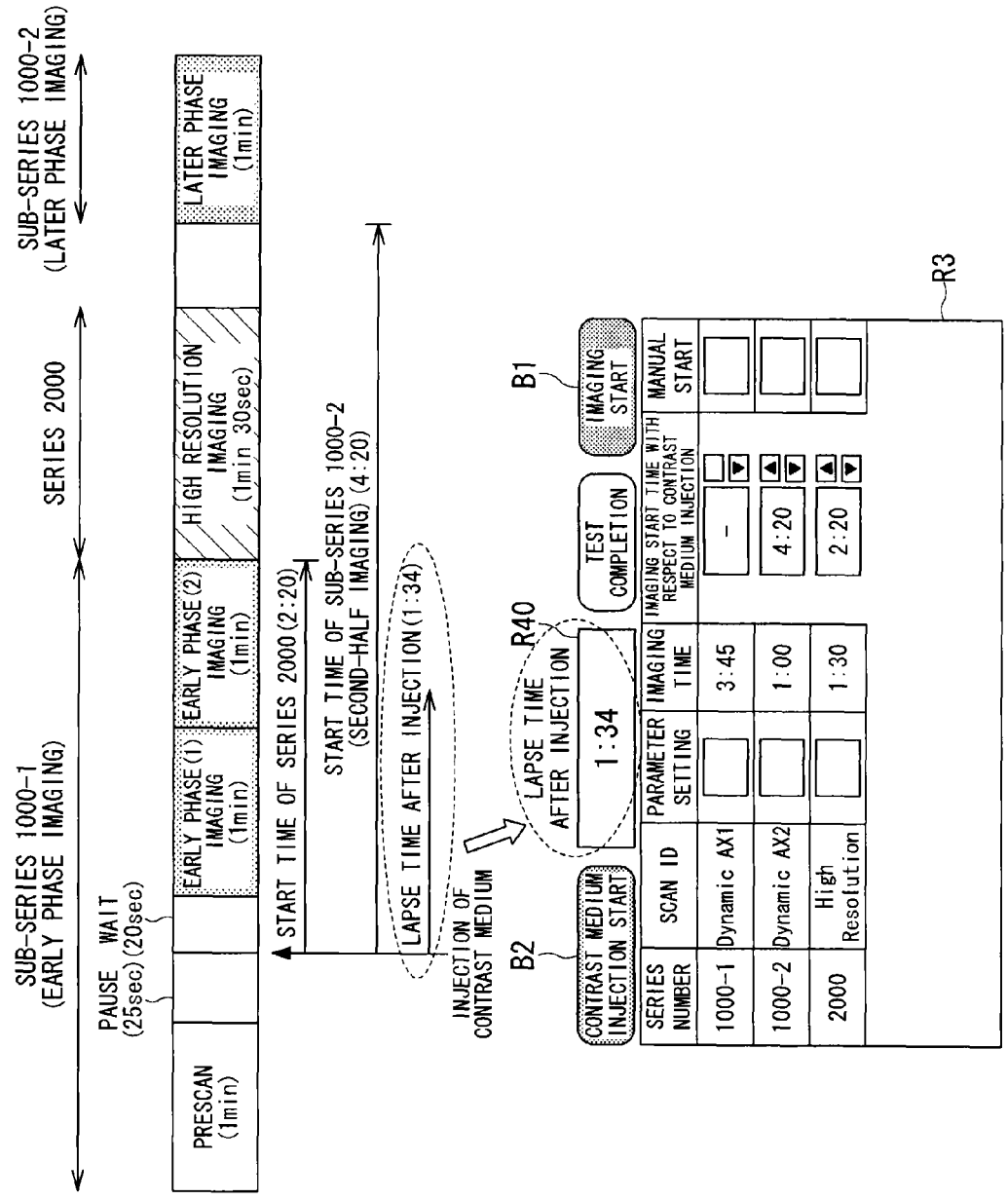
FIGS. 12A and 12B are diagrams showing an example of a display of a lapse time after injection of the contrast medium.

FIGS. 12A and 12B are diagrams for illustrating the execution phase of the single patient composite imaging. The sub-series 1000-1, the series 2000 and the sub-series 1000-2 set as described above are started by clicking the "imaging start" button B1. If the imaging start mode is set to be "automatic", the sub-series 1000-1, whose start time is not set in the "imaging start time with respect to contrast medium injection", is first started.

In the course of execution of the sub-series 1000-1, the "contrast medium injection start" button B2 is clicked, and injection of the contrast medium is started at this point in time. Then, the lapse time after the injection of the contrast medium is displayed in the "lapse time after injection" display field R40. In the example shown in FIGS. 12A and 12B, the lapse time after the injection of the contrast medium is shown as "1:34" (1 minute and 34 seconds).

The conventional magnetic resonance imaging apparatus does not provide any display of the lapse time after the injection of the contrast medium, so that the user has to check the lapse time with a stopwatch or the like separately prepared. However, according to this embodiment, the lapse time after the injection of contrast medium, which is essential in the contrast medium imaging, is always displayed, so that the user, such as a technician responsible for the imaging, can perform the imaging without fault.

When the lapse time after the injection of the contrast medium reaches 2 minutes and 20 seconds (2:20), which is the imaging start time with respect to the contrast medium injection set for the "another imaging" series 2000, the high resolution imaging of the series 2000 is automatically started. The imaging series 2000 automatically ends 1 minutes and 30 seconds after the start thereof. Then, when the lapse time after the injection of the contrast medium reaches 4 minutes and 20 seconds (4:20), which is the imaging start time with respect to the contrast medium injection set for the sub-series 1000-2, the second-half imaging sub-series 1000-2 is automatically started.

The series 2000 and the sub-series 1000-2 are automatically started and automatically ended by the control part 120 (see FIG. 2) automatically controlling the sequence controller 56 based on the settings of the imaging start time setting part 112. As for the other imaging conditions than the imaging start time, the control part 120 controls the sequence controller based on the settings of the imaging condition setting part 111.

As described above, the magnetic resonance imaging apparatus 1 according to this embodiment is configured to set the start time of each series with respect to the lapse time after the injection of the contrast medium and automatically start the imaging at the set start time, so that the magnetic resonance imaging apparatus 1 can perform the contrast medium imaging with high reliability and high time accuracy.

Figure 13:
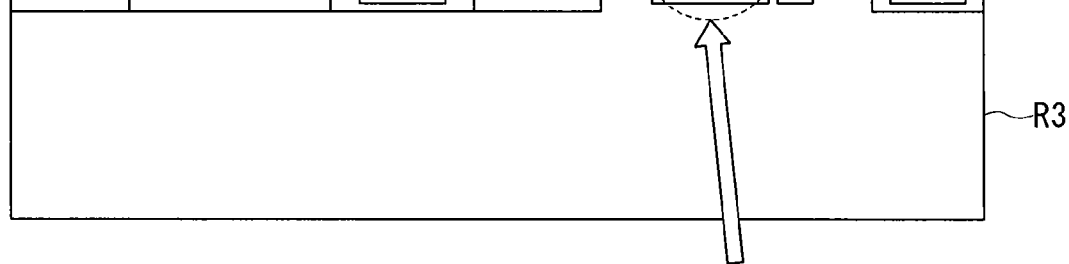
FIG. 13 is a diagram showing an example of a display in which a set imaging start time is updated to an actual imaging start time.

In a case where an imaging sequence is manually started, for example, the actual imaging start time may deviate from the planned (set) imaging start time. In such a case, as shown in FIG. 13, the display of the "imaging start time with respect to contrast medium injection" in the "series information" region R3 may be updated to the actual imaging start time. FIG. 13 shows an example of the display in which the set time (planned time) of the sub-series 1000-2 is 4:20, while the actual start time is 4:22, and the set time (planned time) of the series 2000 is 2:20, while the actual start time is 2:14.

(4) Multiple Patient Composite Imaging

The "single patient composite imaging", in which another imaging of the same patient is inserted in the idle time of the dynamic imaging of a patient, has been described above. In the following, the "multiple patient composite imaging", in which contrast medium imaging is performed on a plurality of patients, will be described.

As described above, in imaging for diagnosis of a liver cell using the recently developed Primovist-based contrast medium, a long waiting time (idle time) of about 20 minutes is required after injection of the contrast medium for Primovist to be absorbed in the liver cell.

Figure 14:
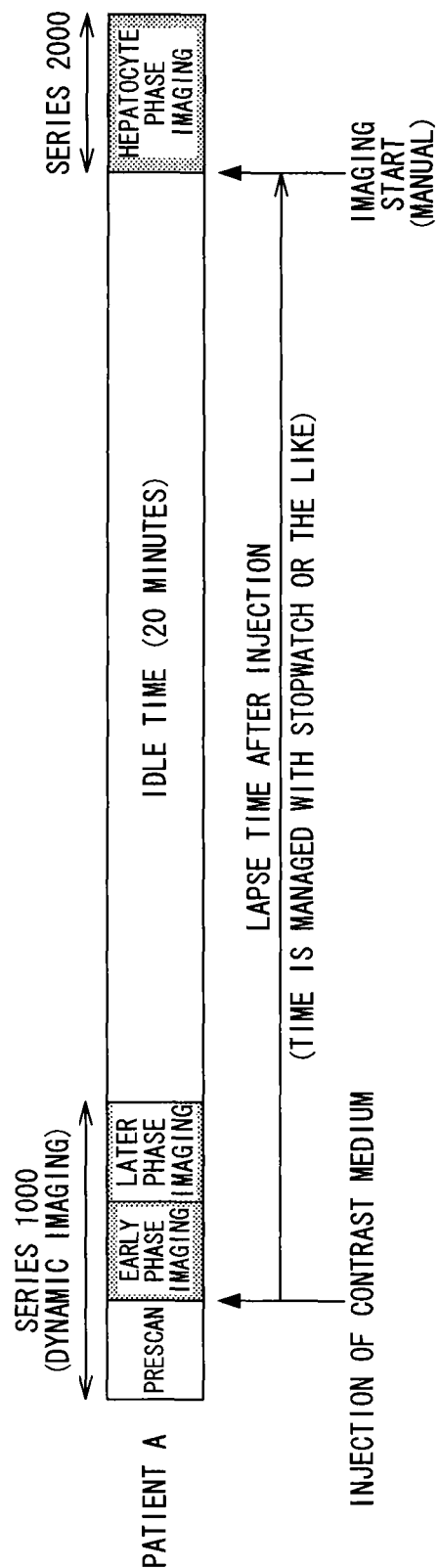
FIG. 14 is a diagram showing an example of a Primovist-based contrast medium imaging sequence.

FIG. 14 is a diagram showing an example of a conventional Primovist-based contrast medium imaging sequence. In the Primovist-based contrast medium imaging, the dynamic imaging involving the early phase imaging and the later phase imaging is performed in an early stage after injection of the contrast medium. After the dynamic imaging, a hepatocyte phase imaging is performed after a waiting time (idle time) of about 20 minutes, which is required for Primovist-based contrast medium to be absorbed in the liver cell.

In the conventional Primovist-based contrast medium imaging, the patient has to stay on the bed and wait for the subsequent hepatocyte phase imaging to start for the idle time of about 20 minutes and thus has to have great patience. Although an attempt has been made to change patients during the idle time of about 20 minutes and perform the same Primovist-based contrast medium imaging on another patient, the magnetic resonance imaging apparatus is not provided with a unit that appropriately manages the lapse time after the injection of the contrast medium. Consequently, the user, such as a technician responsible for the imaging, has to manage the lapse time after the injection of the contrast medium for each patient with a stopwatch or the like.

In the Primovist-based contrast medium imaging described below, the dynamic imaging performed in a relatively early stage after injection of the contrast medium is generally referred to as a first-half imaging and denoted by an identification number "series 1000" as shown in FIG. 14. The hepatocyte phase imaging performed after the idle time of about 20 minutes is referred to as a second-half imaging and denoted by an identification number "series 2000".

Figure 15:
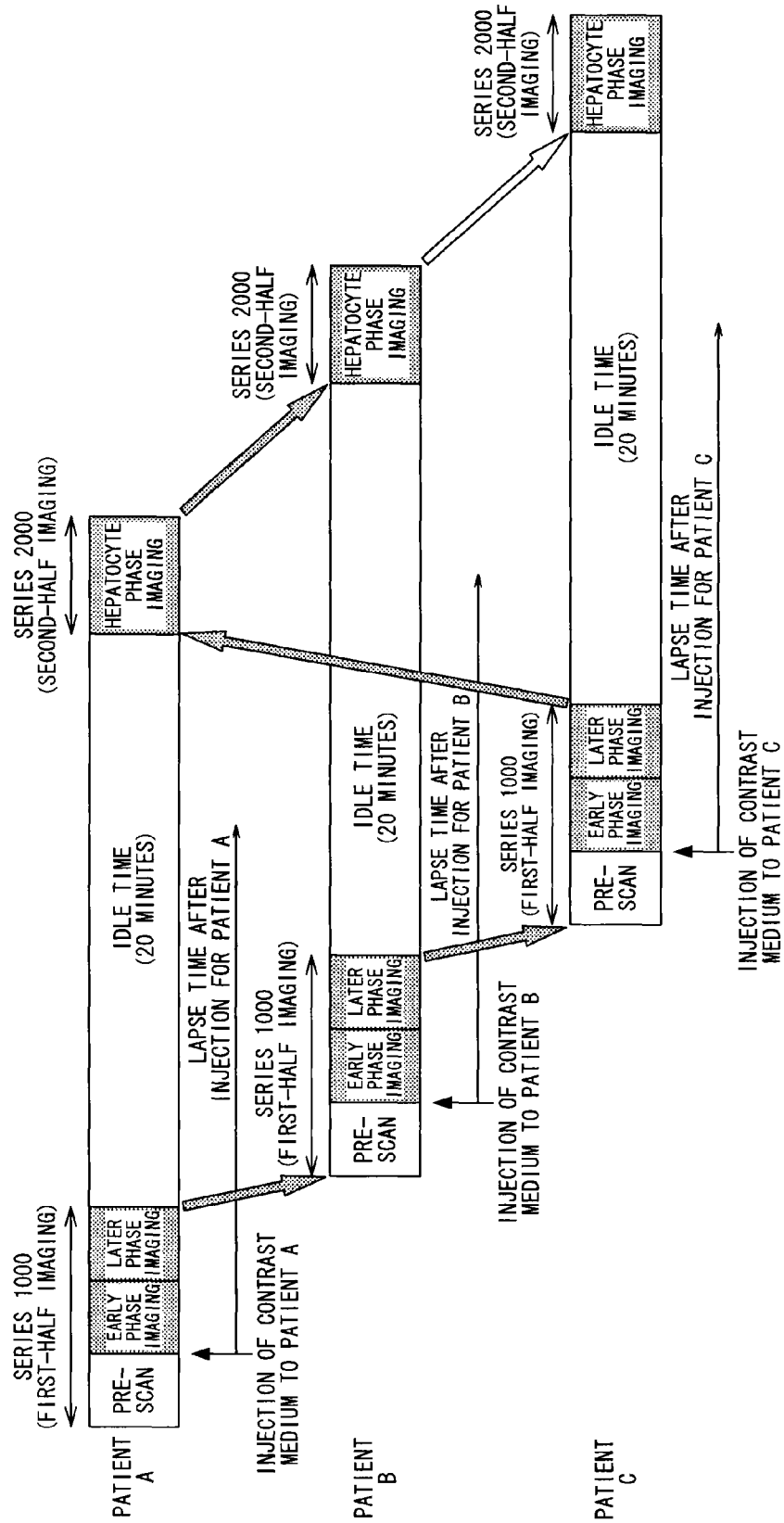
FIG. 15 is a diagram for illustrating an example in which the Primovist-based contrast medium imaging is performed by changing a plurality of patients.

FIG. 15 is a diagram for illustrating an example of the Primovist-based contrast medium imaging performed by changing a plurality of patients. In the following description of this example, it is assumed that the imaging is alternately performed on three patients A, B and C. As shown in FIG. 15, when the first-half imaging of the patient A is completed, the imaging target is changed from the patient A to the patient B, and the first-half imaging of the patient B is performed. When the first-half imaging of the patient B is completed, the imaging target is changed from the patient B to the patient C, and the first-half imaging of the patient C is performed. When the first-half imaging of the patient C is completed, the imaging target is changed from the patient C back to the patient A, and the second-half imaging of the patient A is performed.

The first-half imagings of the patients B and C are performed during the idle time of the imaging of the patient A. Therefore, the idle time can be efficiently used, and the total imaging time of the three patients is substantially reduced compared with the case where the imaging is performed without changing patients. In the Primovist-based contrast medium imaging, too, the start time of the second-half imaging is highly important. The time between the injection of the contrast medium and the start of the second-half imaging varies more or less with the patient but is generally set to be 20 minutes or so. The second-half imaging has to be started with reliability after the idle time of about 20 minutes set for each patient.

The magnetic resonance imaging apparatus 1 according to this embodiment provides a unit that performs the multiple patient composite imaging with reliability as described below.

In the case where the multiple patient composite imaging is to be performed, a plurality of waiting patients are previously registered with the magnetic resonance imaging apparatus 1. For example, as shown in FIG. 15, when the imaging is performed by changing three patients A, B and C, the patients A, B and C are registered with the magnetic resonance imaging apparatus 1. In addition, an imaging condition or the like of each patient is previously set.

Figure 16:
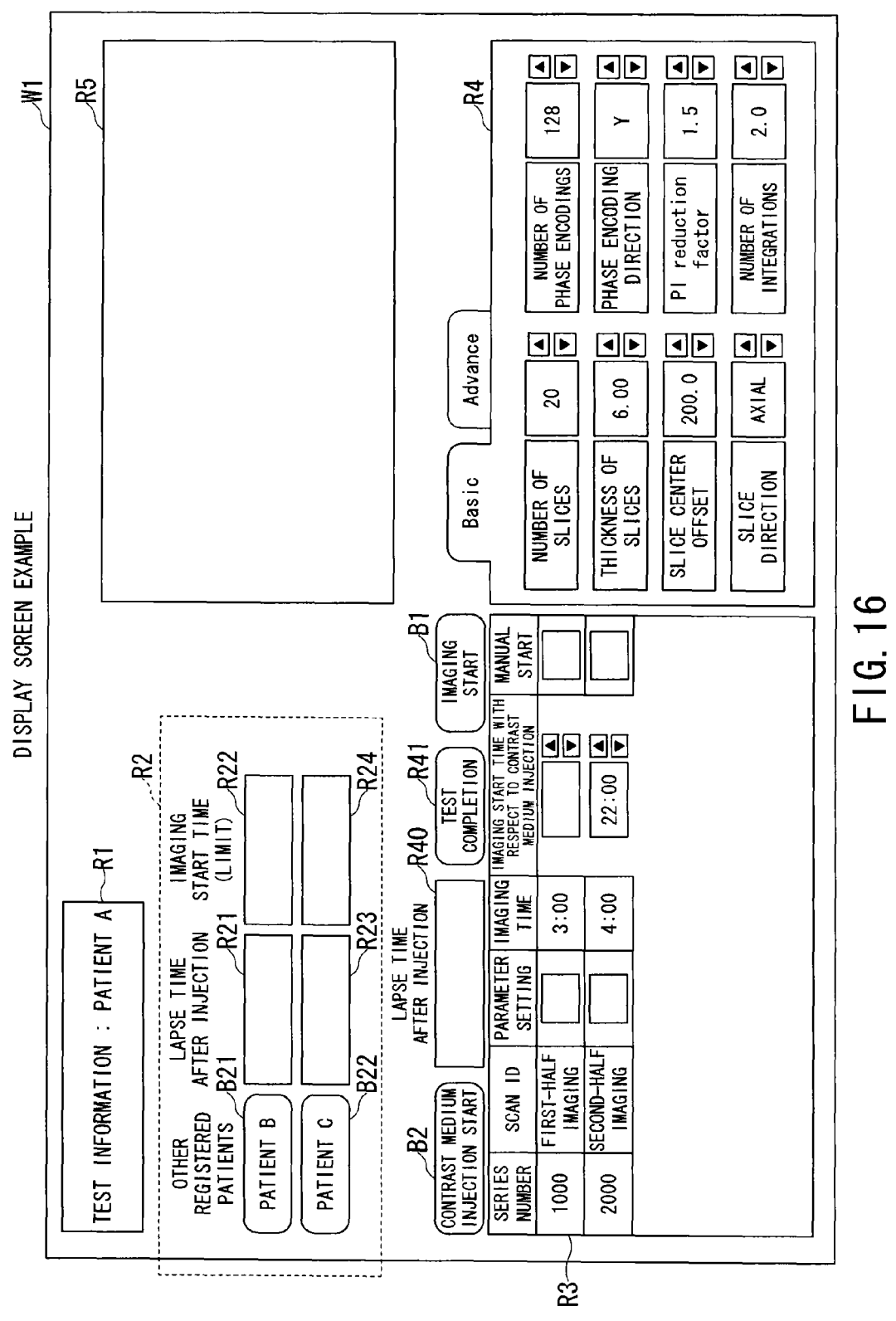

FIG. 16 shows an example of the display on the screen W1 for setting imaging conditions for the patient A, which is basically the same as that in the case of the single patient composite imaging described above. In the case of the Primovist-based contrast medium imaging, in the "series information" region R3, the first-half imaging (dynamic imaging) is set as the series 1000, and the second-half imaging (hepatocyte phase imaging) is set as the series 2000, for example. The imaging start time of the second-half imaging (series 2000) is set to be 22 minutes (22:00) with respect to the time of injection of the contrast medium, for example. The time of 22 minutes is the sum of 2 minutes of the dynamic imaging (1 minute of the early phase imaging and 1 minute of the later phase imaging) performed immediately after injection of the contrast medium and the idle time of 20 minutes until the hepatocyte phase imaging. The imaging conditions (parameters) previously set for each of the series 1000 and 2000 are checked in the "parameter information" region R4 and modified as required.

In the "waiting patient information" region R2, a "patient B" button B21 and a "patient C" button B22 for switching the screen to the screens for the registered patients B and C, respectively, are provided. In the "waiting patient information" region R2, display fields R21 and R23 for displaying the lapse time after the injection of the contrast medium to the patients B and C, respectively, and display fields R22 and R24 for displaying the start time of the second-half imaging with respect to the contrast medium injection to the patients B and C, respectively, are also provided.

To switch the screen to the screen for another registered patient B or C, the "patient B" button B21 or the "patient C" button B22 in the "waiting patient information" region R2 is clicked. As illustrated in FIG. 15, in a case where the same Primovist-based contrast medium imaging as that for the patient A is to be performed on the patients B and C, series and imaging conditions similar to those shown in FIG. 16 are set on the screens for the patients B and C.

Figure 17:
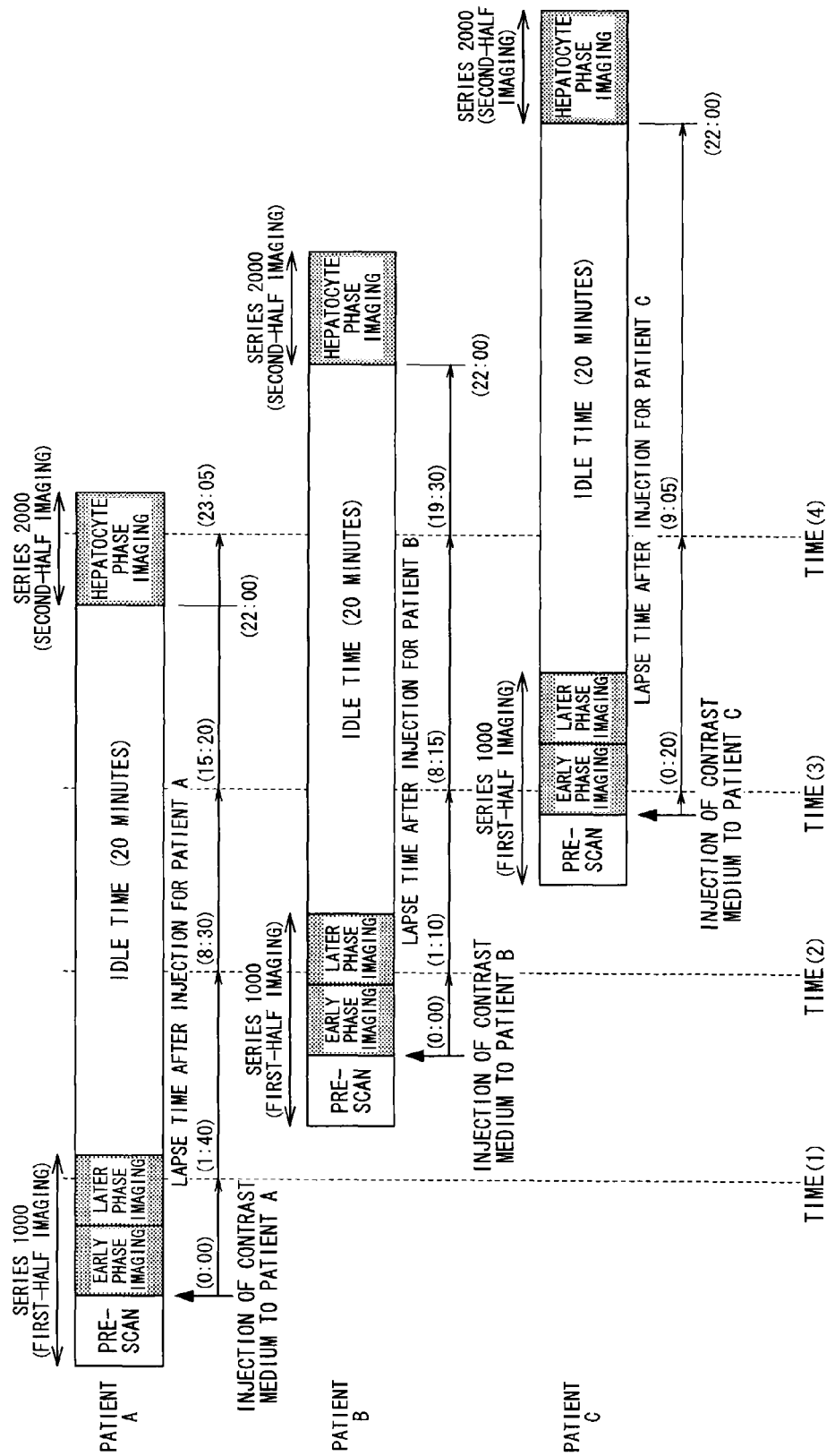
FIG. 17 is a diagram showing a temporal relationship between the entire contrast medium imaging sequence performed by changing three patients and displays on the screen during imaging.

The magnetic resonance imaging apparatus 1 according to this embodiment is characterized in that the apparatus always displays the lapse time after the time of injection of the contrast medium to each patient and the start time of the second-half imaging with respect to the time of contrast medium injection to each patient even when the imaging is performed by changing patients during the idle time of the contrast medium imaging. In the following, the example of the display will be described with reference to FIGS. 17 to 19. FIG. 17 is a diagram showing a relationship among imaging sequences for the patients A, B and C with respect to times (1), (2), (3) and (4). FIGS. 18A, 18B, 19A and 19B show displays of the screen W1 at the times (1), (2), (3) and (4), respectively. In the following, the examples of the displays of the screen W1 at the times (1), (2), (3) and (4) will be described.

Figure 18A:
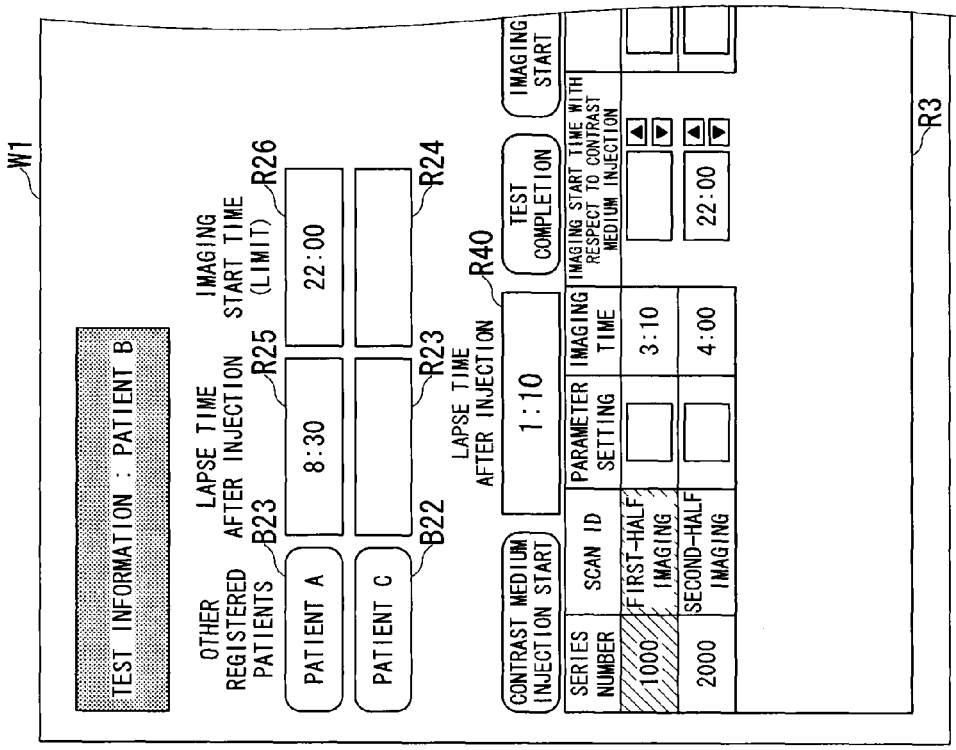
FIGS. 18A and 18B are diagrams showing examples of the display on the screen at a time (1) and a time (2) in FIG. 17.

As shown in the upper part of FIG. 17, the first-half imaging of the contrast medium imaging of the patient A is first started. Prescan is performed, and then the contrast medium is injected. FIG. 18A shows the screen W1 for the patient A at the time (1) when 1 minute and 40 seconds has lapsed after the injection of the contrast medium. In the "lapse time after injection" display field R40, "1:40" is displayed as the lapse time after the injection of the contrast medium to the patient A. At the time (1), the contrast medium has not been injected to the patients B and C, and therefore, the display fields R21 and R23 for displaying the lapse time after the injection of the contrast medium to the patients B and C, respectively, and the display fields R22 and R24 for displaying the start time of the second-half imaging with respect to the contrast medium injection to the patients B and C, respectively, are all blank.

Figure 18B:
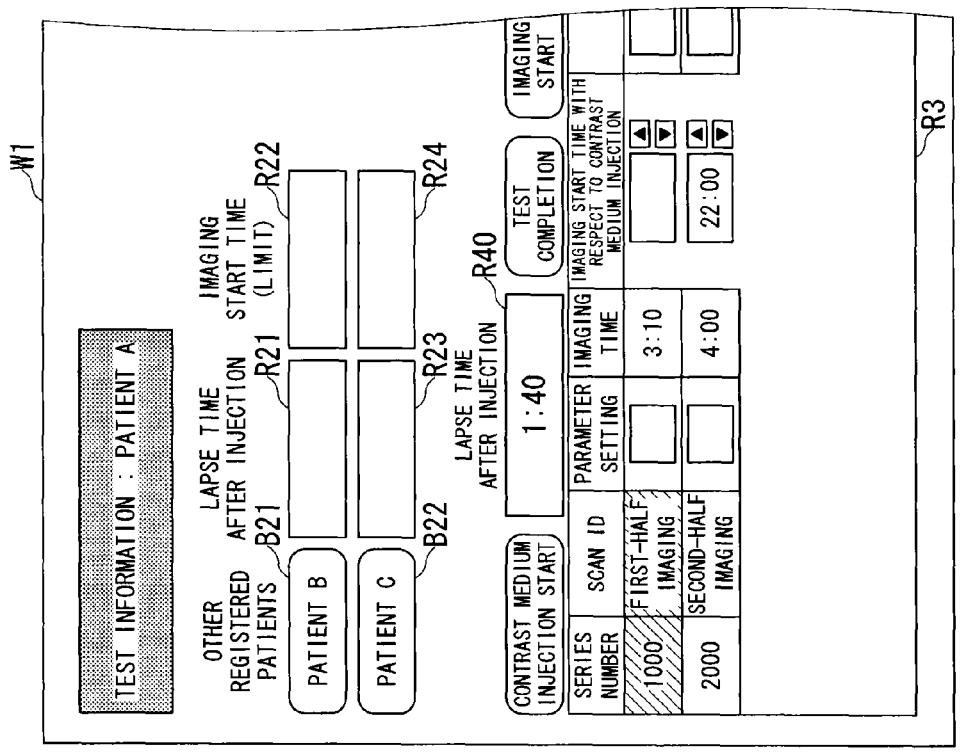

Once the first-half imaging of the patient A is completed, the patient A lying in the magnetic resonance imaging apparatus 1 is replaced with the patient B, and the contrast medium imaging of the patient B is started. Before starting the contrast medium imaging of the patient B, the "patient B" button B21 in the "waiting patient information" region R2 is clicked to switch the entire screen W1 from the screen for the patient A to the screen for the patient B as shown in FIG. 18B. Thus, the patient identification information displayed in the upper left area of the screen W1 is switched from the "patient A" to the "patient B". In the "waiting patient information" region R2, the "patient B" button B21 is switched to the "patient A" button B23, the display field R21 for displaying the lapse time after the injection of the contrast medium to the patient B is switched to the display field R25 for displaying the lapse time after the injection of the contrast medium to the patient A, and the display field R22 for displaying the start time of the second-half imaging of the patient B is switched to the display field R26 for displaying the start time of the second-half imaging of the patient A.

For the patient B, as in the case of the patient A, prescan is performed, and then the contrast medium is injected. FIG. 18B shows the screen W1 for the patient B at the time (2) when 1 minute and 10 seconds has lapsed after the injection of the contrast medium. In the "lapse time after injection" display field R40, "1:10" is displayed as the lapse time after the injection of the contrast medium to the patient B.

At the time (2), the contrast medium has already been injected to the patient A, and the lapse time after the injection of the contrast medium for the patient A is increasing independently of the patient B. For example, at the time (2), the lapse time after the injection of the contrast medium for the patient A is 8 minutes and 30 seconds, as shown in FIG. 17. Thus, "8:30" is displayed in the display field R25 in the "waiting patient information" region R2 for displaying the lapse time after the injection of the contrast medium to the patient A. In the display field R26 adjacent to the display field R25, "22:00" is displayed as the start time of the second-half imaging of the patient A with respect to the contrast medium injection to the patient A.

At the time (2), the contrast medium has not been injected to the patient C, and therefore, the display fields R23 and R24 are still blank.

Once the first-half imaging of the patient B is completed, the patient B lying in the magnetic resonance imaging apparatus 1 is replaced with the patient C, and the contrast medium imaging of the patient C is started. Again, before starting the contrast medium imaging of the patient C, the "patient C" button B22 in the "waiting patient information" region R2 is clicked to switch the entire screen W1 from the screen for the patient B to the screen W1 for the patient C as shown in FIG. 19A. Thus, the patient identification information displayed in the upper left area of the screen W1 is switched from the "patient B" to the "patient C". In the "waiting patient information" region R2, the "patient C" button B22 is switched to the "patient B" button B21, the display field R23 for displaying the lapse time after the injection of the contrast medium to the patient C is switched to the display field R21 for displaying the lapse time after the injection of the contrast medium to the patient B, and the display field R24 for displaying the start time of the second-half imaging of the patient C is switched to the display field R22 for displaying the start time of the second-half imaging of the patient B.

For the patient C, as in the cases of the patients A and B, prescan is performed, and then the contrast medium is injected. FIG. 19A shows the screen W1 for the patient C at the time (3) when 20 seconds has lapsed after the injection of the contrast medium. In the "lapse time after injection" display field R40, "0:20" is displayed as the lapse time after the injection of the contrast medium to the patient C.

At the time (3), the contrast medium has already been injected to all the registered patients A, B and C. For example, at the time (3), the lapse time after the injection of the contrast medium for the patient A is 15 minutes and 20 seconds, and the lapse time after the injection of the contrast medium for the patient B is 8 minutes and 15 seconds, as shown in FIG. 17. Thus, "15:20" is displayed in the display field R25 in the "waiting patient information" region R2 for displaying the lapse time after the injection of the contrast medium to the patient A, and "8:15" is displayed in the display field R21 for displaying the lapse time after the injection of the contrast medium to the patient B. And "22:00" is displayed in both the display fields R26 and R22 for displaying the start time of the second-half imaging with respect to the time of contrast medium injection to the patients A and B.

Once the first-half imaging of the patient C is completed, the imaging target of the magnetic resonance imaging apparatus 1 is changed from the patient C back to the patient A, and the second-half imaging of the patient A is started. FIG. 19B shows the screen W1 at the time (4) when imaging of the patient A is being performed. At the time (4), 23 minutes and 5 seconds has lapsed after the injection of the contrast medium to the patient A, and "23:05" is displayed in the "lapse time after injection" display field R40 as the lapse time after the injection of the contrast medium to the patient A.

On the other hand, at the time (4), the lapse time after the injection of the contrast medium to the patient B is 19 minutes and 30 seconds, and the lapse time after the injection of the contrast medium to the patient C is 9 minutes and 5 seconds. Therefore, in the "waiting patient information" region R2, "19:30" is displayed in the display field R21 for displaying the lapse time after the injection of the contrast medium to the patient B, and "9:05" is displayed in the display field R23 for displaying the lapse time after the injection of the contrast medium to the patient C.

As described above, the magnetic resonance imaging apparatus 1 according to this embodiment is configured to always display not only the lapse time after the injection of the contrast medium for the patient currently being imaged but also the lapse times after the injection of the contrast medium for the waiting patients in the screen W1 when performing the contrast medium imaging by changing a plurality of patients. Therefore, the operation of managing the lapse time for each patient with a stopwatch or the like that is conventionally be required is unnecessary, and time management can be conducted with reliability.

The start time of the second-half imaging of each patient is displayed, as a limit, next to the lapse time after injection of the contrast medium to each patient. Therefore, the contrast medium imaging of a plurality of patients can be performed as planned by constantly checking the time remaining until the start of the second-half imaging of each patient.

In the case where the contrast medium imaging is performed by changing a plurality of patients, the imaging may not proceed as planned because it takes longer than expected to change patients or for other reasons. For example, when the first-half imaging of the patient B (a second patient) is being performed in the idle time after the first-half imaging of the patient A (a first patient), the start time of the second-half imaging of the patient A may approach.

In view of such a situation, the magnetic resonance imaging apparatus 1 according to an aspect of this embodiment is configured so that the determination part 130 of the magnetic resonance imaging apparatus 1 determines whether or not the second-half imaging of the first patient can be started at the set start time during or immediately after the first-half imaging of the second patient, and provides an alarm indication if the determination part 130 determines that the second-half imaging of the first patient cannot be started at the set start time.

Figure 20:
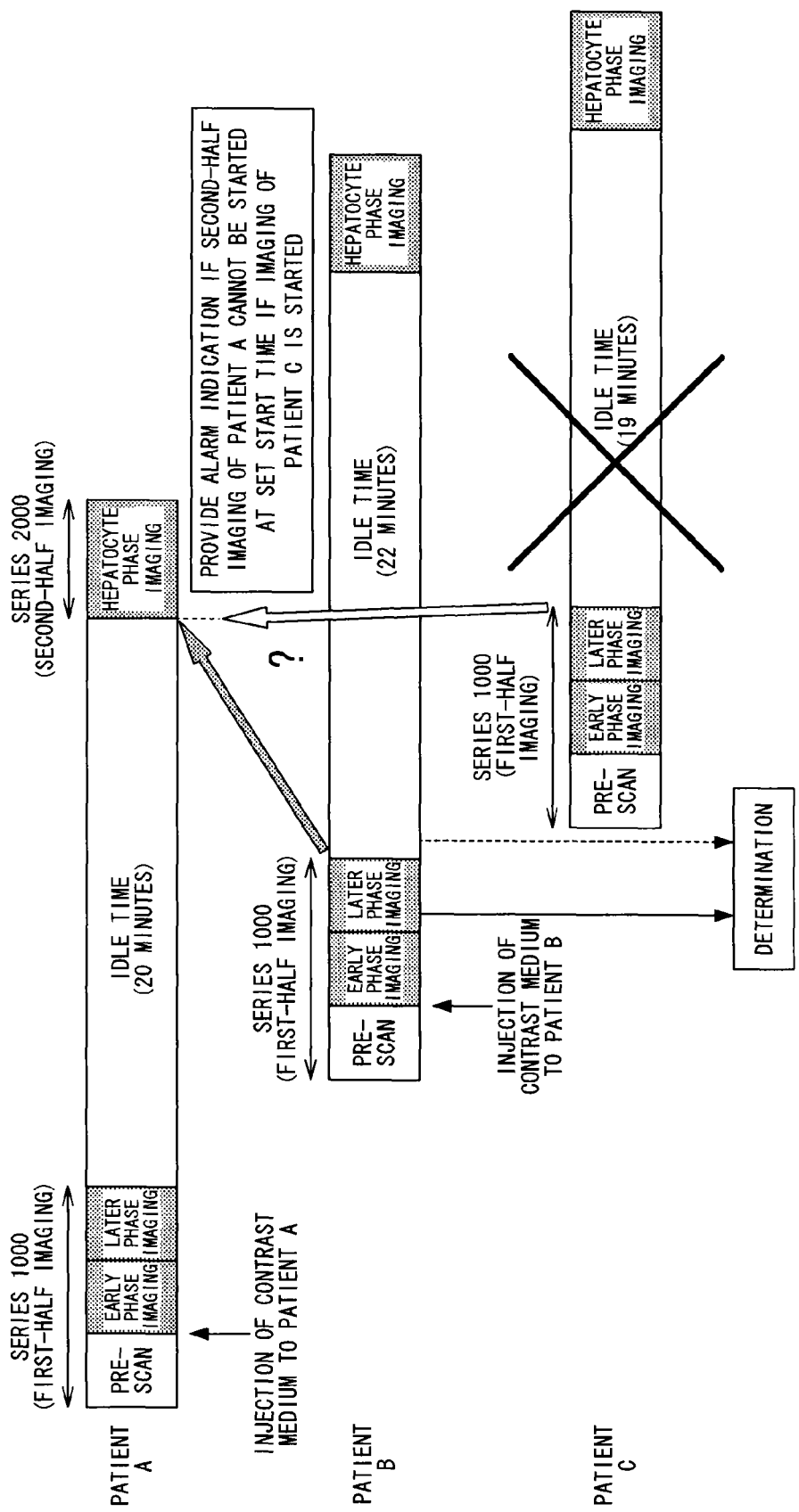
FIG. 20 is a diagram for illustrating an example of an operation of determination of whether or not a second-half imaging can be started at a set start time.

FIG. 20 is a diagram showing an example of this implementation. In the example shown in FIG. 20, the solid line shows the case where the determination is made during imaging of the patient B, and the dashed line shows the case where the determination is made after imaging of the patient B. In the case where the determination is made during imaging of the patient B, the completion time of the first-half imaging of the patient B is expected, the time required to change the patient from the patient B to the patient C is estimated, and it is determined whether or not the second-half imaging of the patient A can be started at the set start time if the first-half imaging of the patient C is started after the first-half imaging of the patient B. If it is determined that the second-half imaging of the patient A cannot be started at the set start time, an alarm indication is provided.

On the other hand, in the case where the determination is made after imaging of the patient B, the determination is made when the "patient C" button B22 for switching the imaging screen W1 to the screen for the patient C is clicked, for example. At this point in time, if it is determined that the second-half imaging of the patient A cannot be started at the set start time, an alarm indication is displayed in an area of the screen W1. On seeing the alarm indication, the technician decides not to start the imaging of the patient C and starts the imaging of the patient A.

When the imaging of the second patient is being performed during the idle time after the first-half imaging of the first patient, information on how long time remains for changing patients to perform the second-half imaging of the first patient is also essential for the technician who manages the imaging.

Figure 21:
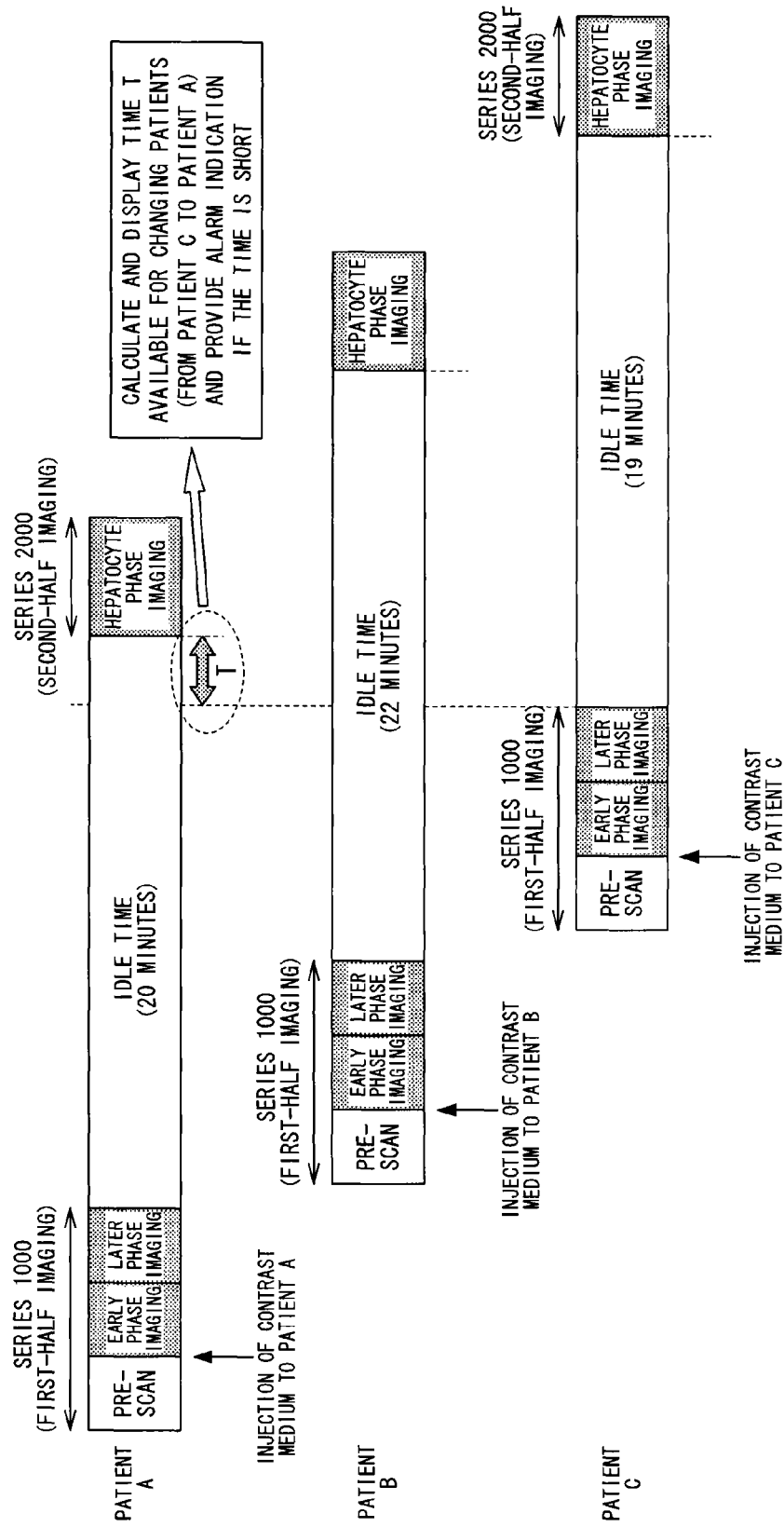
FIG. 21 is a conceptual diagram for illustrating calculation of a time available for changing patients.
Figure 22:
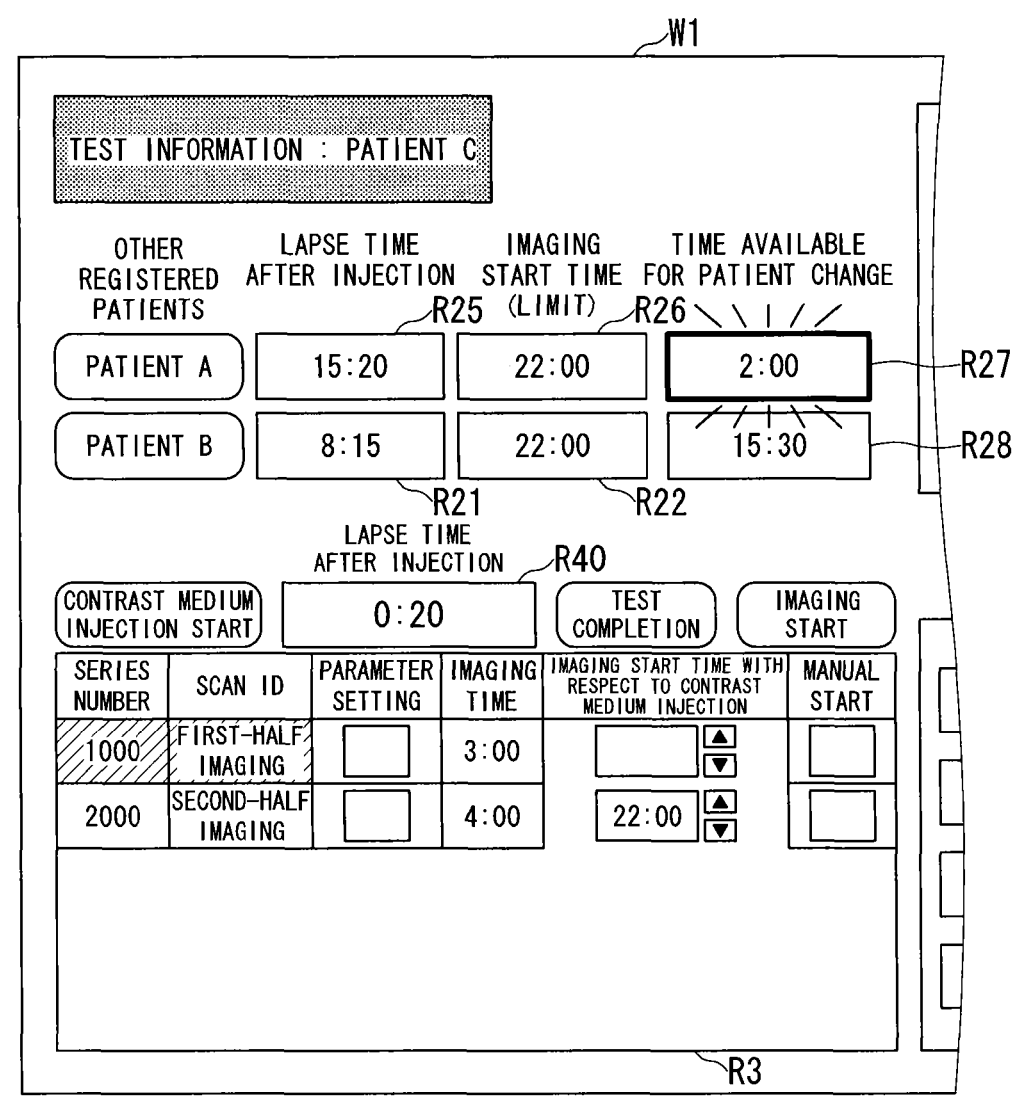

Thus, according to an aspect of this embodiment, the time available for changing patients is calculated and displayed. FIGS. 21 and 22 are diagrams an example of the calculation and display operations. In the example shown in FIGS. 21 and 22, the time available for changing the patient from the second patient (patient C) to the first patient (patient A) is calculated from the difference between the expected completion time of the first-half imaging of the patient (the second patient, the patient C in the example shown in FIGS. 21 and 22) after patient change and the start time of the second-half imaging of the first patient set by the setting part, and the calculated time is displayed. The time available for patient change is displayed in display fields R27 and R28 at the right end of the "waiting patient information" region R2 as illustrated in FIG. 22, for example. For example, in a case where the patient is changed from the patient C to the patient A after completion of the first-half imaging of the patient C, 2 minutes ("2:00") is displayed as the time available for the patient change. In a case where the patient is changed from the patient C to the patient B after completion of the first-half imaging of the patient C, 15 minutes and 30 seconds ("15:30") is displayed as the time available for the patient change.

If it is determined that the calculated time available for patient change is less than a standard patient change time, an alarm indication is provided. For example, if it is determined that the time available for changing the patient to the patient A is 2 minutes, which is less than 3 minutes, which is the standard patient change time, an alarm is provided by making the time available for patient change blink. This alarm indication can help enable the second-half imaging of the patient A to be stated at the set start time if the change from the patient C to the patient A is quickened on seeing the alarm indication.

As described above, the magnetic resonance imaging apparatus 1 according to this embodiment can perform time management and imaging condition management for combining a plurality of series of imagings or imagings of a plurality of patients with high efficiency and high reliability and can efficiently use the waiting time (idle time) involved in the contrast medium imaging. As a result, the total imaging time can be reduced, and the burden on the patients can be reduced.

Although embodiments of the present invention have been described above, these embodiments are provided only for the illustrative purposes and are not intended to limit the scope of the invention. The embodiments can be implemented in various other forms, and various omissions, replacements and modifications can be made without departing the spirit of the invention. These embodiments and various modifications thereof are included not only in the scope and spirit of the invention but also in the scope of the invention described in the claims and equivalents thereof.

What is claimed is:

1. A magnetic resonance imaging apparatus that performs a contrast medium imaging, comprising:
    circuitry configured to
        measure and manage a lapse time after injection of a contrast medium,
        divide an original imaging series performing the contrast medium imaging and including (i) a first-half imaging performed as an early-phase contrast imaging after the injection of the contrast medium, (ii) an idle time provided after the first-half imaging, and (iii) a second-half imaging performed as a late-phase contrast imaging after the idle time, into a first-half imaging series and a second-half imaging series excluding the idle time, the first-half imaging series and the second-half imaging series respectively corresponding to the first-half imaging and the second-half imaging in the original imaging series,
        set a start time for the second-half imaging series in the form of the lapse time after injection of the contrast medium,
        insert another imaging series, different from the original imaging series, between the first-half imaging series and the second-half imaging series, by setting a start time for the another imaging series in the form of the lapse time such that the start time for the another imaging series is earlier than the start time of the second-half imaging series, and
        perform control to start the another imaging series after the first-half imaging series in accordance with the start time set for the another imaging series, and to start the second-half imaging series after the another imaging series in accordance with the start time set for the second-half imaging series; and
    a display that displays at least the measured lapse time and the set start time,
    wherein the first-half imaging series and the second-half imaging series are performed on a first patient and the another imaging series is performed on a second patient.

2. The magnetic resonance imaging apparatus according to claim 1, wherein the set start time of the second-half imaging series is changeable by a user operation.

3. The magnetic resonance imaging apparatus according to claim 1, wherein the display displays the start time of the another imaging and the start time of the another imaging is changeable by a user operation.

4. The magnetic resonance imaging apparatus according to claim 1, wherein the circuitry manages the first-half imaging series and the second-half imaging series resulting from the division as one group, and automatically reflects a modification to an imaging condition of any one of imagings in the group in the imagings other than the imaging whose imaging condition is modified.

5. The magnetic resonance imaging apparatus according to claim 1, wherein the display provides an alarm indication if an imaging time of the another imaging is longer than the idle time.

6. The magnetic resonance imaging apparatus according to claim 1, wherein, when an imaging time of the another imaging is longer than the idle time, the circuitry automatically adjusts a value of a parameter of an imaging condition of the another imaging to make the imaging time of the another imaging equal to or less than the idle time.

7. The magnetic resonance imaging apparatus according to claim 6, wherein the circuitry refers to a preset order of precedence among types of parameters and preset lower limit values of the parameters and reduces the values of the parameters to the respective lower limits one by one in the order of precedence to make the imaging time of the another imaging equal to or less than the idle time.

8. The magnetic resonance imaging apparatus according to claim 7, wherein the types of parameters include at least one of a number of phase encodings, a reduction factor of the number of phase encodings in a parallel imaging, a number of slices, and an excitation pulse interval.

9. The magnetic resonance imaging apparatus according to claim 7, wherein the display provides an alarm indication when the imaging time of the another imaging does not become equal to or less than the idle time even after the values of all the parameters of the types of parameters are reduced to the respective lower limits.

10. The magnetic resonance imaging apparatus according to claim 1, wherein in a case where the contrast medium imaging is performed on a plurality of patients, including the first patient and the second patient, by changing patients,
    the circuitry measures and manages the lapse time after injection of the contrast medium for each of the patients, sets an imaging condition for each patient, and sets the start time of the second-half imaging series of each patient in the form of a lapse time after injection of the contrast medium to the patient, and
    the display part switches, when a patient change occurs, a display from an imaging condition of the patient before the patient change to an imaging condition of the patient after the patient change and always displays the lapse time after injection of the contrast medium for each patient and the start time of the second-half imaging series with respect to the time of injection of the contrast medium for each patient even after the patient change.

11. The magnetic resonance imaging apparatus according to claim 10, wherein the contrast medium imaging of each said patient is performed by performing the first-half imaging series of the first patient, replacing from the first patient with the second patient, performing a first-half imaging of the another imaging series of the second patient in the idle time for the first patient, and performing the second-half imaging series of the first patient after the first-half imaging of the second patient is completed.

12. The magnetic resonance imaging apparatus according to claim 11,
    wherein the circuitry is configured to determine whether or not the second-half imaging series of the first patient is to be started at the set start time, and
    wherein the display provides an alarm indication when it is determined that the second-half imaging series of the first patient is not to be started at the set start time.

13. The magnetic resonance imaging apparatus according to claim 11,
  wherein the circuitry is configured to determine a time available for changing the patient from the second patient to the first patient based on an expected completion time of the first-half imaging series of the second patient and the set start time of the second-half imaging series of the first patient, and
  wherein the display displays the determined time available for changing.

14. The magnetic resonance imaging apparatus according to claim 1, wherein the contrast medium imaging is a dynamic imaging using a gadolinium contrast medium, and the first-half imaging series includes one or more early phase imagings, and the second-half imaging series is a later phase imaging.

15. The magnetic resonance imaging apparatus according to claim 10, wherein the contrast medium imaging is an imaging using a liver cell diagnosis contrast medium, the first-half imaging series includes one or more dynamic imagings, and the second-half imaging series is a hepatocyte phase imaging.

\* \* \* \* \*